United States Patent
DiAngelo et al.

(10) Patent No.: US 11,213,419 B2
(45) Date of Patent: Jan. 4, 2022

(54) DISTRACTIVE AND MOBILITY-ENABLING LUMBAR SPINAL ORTHOSIS DEVICES, SYSTEMS, AND METHODS FOR TREATING MECHANICAL LOW BACK PAIN

(71) Applicant: University of Tennessee Research Foundation, Knoxville, TN (US)

(72) Inventors: Denis J. DiAngelo, Germantown, TN (US); Daniel Clay Hillyard, Arlington, TN (US); Chloe Chung, Lakeland, TN (US); Daniel Hoyer, Memphis, TN (US)

(73) Assignee: University of Tennessee Research Foundation, Knoxville, TN (US)

( * ) Notice: Subject to any disclaimer, the term of this patent is extended or adjusted under 35 U.S.C. 154(b) by 0 days.

(21) Appl. No.: 16/497,322

(22) PCT Filed: Apr. 5, 2018

(86) PCT No.: PCT/US2018/026248
§ 371 (c)(1),
(2) Date: Sep. 24, 2019

(87) PCT Pub. No.: WO2018/187566
PCT Pub. Date: Oct. 11, 2018

(65) Prior Publication Data
US 2020/0375778 A1    Dec. 3, 2020

Related U.S. Application Data

(60) Provisional application No. 62/481,742, filed on Apr. 5, 2017.

(51) Int. Cl.
*A61F 5/02*     (2006.01)
*A61F 5/048*    (2006.01)
*A61H 1/02*     (2006.01)

(52) U.S. Cl.
CPC .............. *A61F 5/048* (2013.01); *A61F 5/028* (2013.01); *A61H 1/0292* (2013.01);
(Continued)

(58) Field of Classification Search
CPC .. A61F 13/12; A61F 13/14; A61F 5/03; A61F 5/05816; A61F 5/3707;
(Continued)

(56) References Cited

U.S. PATENT DOCUMENTS 3,156,430 A    11/1964  Zivi
3,889,664 A     6/1975  Heuser et al.
(Continued)

FOREIGN PATENT DOCUMENTS

WO    WO 2006/090380 A2    8/2006
WO    WO 2018/106679 A1    6/2018

OTHER PUBLICATIONS

Disc Disease Solutions (DDS) 500 Lumbar Decompression Brace with Panels, http://discdiseasesolutions.com/products/dds-500-back-brace/, webpage, accessed May 10, 2021.
(Continued)

*Primary Examiner* — Ophelia A Hawthorne
(74) *Attorney, Agent, or Firm* — Jenkins, Wilson, Taylor & Hunt, P.A.

(57) ABSTRACT

The present subject matter relates to orthotic devices, systems, and methods configured to support a lumbar spine. In some embodiments, a lumbar spinal orthosis system includes a torso belt configured to be secured about a torso of a user, a pelvic belt configured to be secured about a pelvis of the user, and a distractive force mechanism connected between the torso belt and the pelvic belt. The distractive force mechanism is configured to generate a force between the torso belt and the pelvic belt acting bi-directionally across a lumbar spine of the user to substantially
(Continued)

offload bodyweight of the user passing through the lumbar spine.

24 Claims, 22 Drawing Sheets

(52) U.S. Cl.
CPC ............... *A61H 2201/0192* (2013.01); *A61H 2201/1238* (2013.01); *A61H 2201/165* (2013.01); *A61H 2201/1623* (2013.01); *A61H 2201/1628* (2013.01); *A61H 2201/1664* (2013.01)

(58) Field of Classification Search
CPC .......... A61F 5/012; A61F 5/024; A61F 5/026; A61F 5/028; A61F 5/00; A61F 2007/0009; A61F 5/055; A61F 5/05891; A42B 3/0473; A47C 7/383
See application file for complete search history.

(56) References Cited

U.S. PATENT DOCUMENTS

| | | | |
|---|---|---|---|
| 4,202,327 | A | 5/1980 | Glancy |
| 4,483,330 | A | 11/1984 | Jacobsen et al. |
| 4,688,559 | A | 8/1987 | Vito et al. |
| 4,790,301 | A | 12/1988 | Silfverskiold |
| 5,462,518 | A | 10/1995 | Hatley et al. |
| 5,472,410 | A | 12/1995 | Hamersly |
| 6,776,767 | B2 | 8/2004 | Reinecke et al. |
| 7,070,572 | B2 | 7/2006 | Reinecke et al. |
| 7,445,608 | B2 | 11/2008 | Dunfee et al. |
| 7,591,797 | B2 | 9/2009 | Hakonson et al. |
| 8,012,113 | B2 | 9/2011 | Lee et al. |
| 8,657,769 | B2 | 2/2014 | Ingimundarson et al. |
| 8,845,566 | B2 | 9/2014 | Johnson et al. |
| 9,480,593 | B2 | 11/2016 | DiAngelo et al. |
| 2004/0073150 | A1 | 4/2004 | Roballey |
| 2005/0010150 | A1 | 1/2005 | Firsov |
| 2006/0079821 | A1 | 4/2006 | Rauch |
| 2011/0295170 | A1 | 12/2011 | Laranjeira Gomes et al. |
| 2012/0253251 | A1 | 10/2012 | Thornton |
| 2014/0276308 | A1* | 9/2014 | DiAngelo ............... A61F 5/03 602/19 |
| 2015/0231017 | A1 | 8/2015 | Kazemi Banyhashemi |
| 2016/0296361 | A1 | 10/2016 | Leake et al. |
| 2019/0314186 | A1 | 10/2019 | DiAngelo et al. |

OTHER PUBLICATIONS

International Search Report and Written Opinion corresponding to International Patent Application No. PCT/US2017/064696 dated Feb. 22, 2018.
International Search Report corresponding to International Patent Application No. PCT/US2018/026248 dated Jun. 19, 2018.
International Preliminary Report on Patentability (Chapter 1 of the Patent Cooperation Treaty) corresponding to International Patent Application No. PCT/US2017/064696 dated Jun. 20, 2019.
IPRP and Written Opinion corresponding to International Patent Application No. PCT/US2018/026248 dated Oct. 8, 2019.
Wong et al., "Biomechanical evaluation of the Milwaukee brace," Prosthet Orthot Int., vol. 22, No. 1, pp. 54-67 (1998).
Zeh et al., "The flexible TriacTM-Brace for conservative treatment of idiopathic scoliosis. An alternative treatment option?" Acta Orthop Belg., vol. 74, No. 4, pp. 512-521 (2008).
Bernard et al. "The carbon brace," Scoliosis, vol. 8, No. 3, pp. 1-19 (2013).
Notification Concerning Availability of the Publication of the International Application corresponding to International Application No. PCT/US2017/064696 dated Jun. 14, 2018.

Akay et al., "Ant Colony Optimization Approach for Classification of Occupational Low Back Disorder Risks," Hum Factors Ergon Manuf, vol. 19, pp. 1-14 (2009).
Apfel, "Restoration of disk height through non-surgical spinal decompression is associated with decreased discogenic low back pain: a retrospective cohort study," BMC Muscluoskelet Disord, vol. 11, pp. 1-6 (2010).
Baena-Beato, "Effects of Different Frequencies (2-3 Days/Week) of Aquatic Therapy Program in Adults with Chronic Low Back Pain. A Non-Randomized Comparison Trial," Pain Med, vol. 14, pp. 145-158, 2013.
Bigos et al., "Acute low back problems in adults. Clinical practice guidelines No. 14," P. H. S. US Department of Health and Human Services, Agency for Health Care Policy and Research, Ed., ed, 167 pages (1994).
Brecher, "Editor's Message," JAOA, vol. 101, No. 4, 2 pages (2001).
Brown et al., "Sensory and sympathetic innervation of the vertebral endplate in patients with degenerative disc disease," J Bone Joint Surg, vol. 79-B, No. 1, pp. 147-153 (1997).
Childs et al., "Responsiveness of the Numeric Pain Rating Scale in Patient with Low Back Pain," Spine, vol. 30, No. 11, pp. 1331-1334 (2005).
Chou, "Low back pain (chronic)," BMJ Clinical Evidence, vol. 10, pp. 1-41 (2010).
DiAngelo et al., "A novel distractive and mobility-enabling lumbar spinal orthosis," Journal of Rehabilitation and Assistive Technologies Engineering, vol. 3, pp. 1-10 (2016).
DiAngelo et al., "Robotized Method for Comparative Testing of Back Support Devices," Journal of Mississippi Academy of Sciences, pp. 179-186 (2015a).
DiAngelo et al., "Towards the Design of a Distractive and Mobility-Enabling Back Support Device," Journal of Mississippi Academy of Sciences, pp. 193-200 (2015b).
Dundar et al., "Clinical Effectiveness of Aquatic Exercise to Treat Chronic Low Back Pain: A Randomized Controlled Trial," Spine, vol. 34, No. 14, pp. 1436-1440 (2009).
Ferrara et al., "A biomechanical assessment of disc pressures in the lumbosacral spine in response to external unloading forces," Spine J, vol. 5, pp. 548-553, 2005.
Fritzell et al., "2001 Volvo Award Winner in Clinical Studies: Lumbar Fusion Versus Nonsurgical Treatment for Chronic Low Back Pain: A Multicenter Randomized Controlled Trial from the Swedish Lumbar Spine Study Group," Spine, vol. 26, No. 23, pp. 2521-2534 (2001).
Hagg et al., "The clinical importance of changes in outcome scores after treatment for chronic low back pain," Eur Spine J, vol. 12, pp. 12-20 (2003).
Hoy et al., "The global burden of low back pain: estimates from the Global Burden of Disease 2010 Study," Ann Rheum Dis, vol. 73, pp. 968-974 (2014).
Jensen, "Biomechanics of the lumbar intervertebral disk: a review," Phys Ther, vol. 60, No. 6, pp. 765-773 (1980).
Johnson et al., "Active Spinal Orthosis to Reduce Lumbar Postural Muscle Activity in Flexed Postures," JPO, vol. 28, No. 3, pp. 109-113 (2016).
Kawchuk et al., "A non-randomized clinical trial to assess the impact of nonrigid, inelastic corsets on spine function in low back pain participants and asymptomatic controls," Spine J, vol. 15, pp. 2222-2227 (2015).
Koes et al., "Diagnosis and treatment of low back pain," BMJ, vol. 332, pp. 1430-1434 (2006).
Leake. The VerteCore Lift, vertecorelift. Available: https://vertecorelift.wordpress.com/how-vertecore-lift-works/; accessed May 11, 2021.
Mirovsky et al., "The effect of ambulatory lumbar traction combined with treadmill on patients with chronic low back pain," J Back Musculoskelet Rehabil, vol. 19, pp. 73-78 (2006).
Pensri et al., "Biopsychological Factors and Perceived Disability in Saleswomen with Concurrent Low Back Pain," Saf Health Work, vol. 1, pp. 149-157 (2010).
Simmons, "Development of a Mobility-Enabling Spinal Orthosis and Methods for Evaluating and Developing Spinal Orthoses on a

(56) References Cited

OTHER PUBLICATIONS

Robotic Platform," PhD, UTHSC Orthopedic Surgery & Biomedical Engineering, The University of Tennessee Health Science Center, 93 pages (2014).
Stubbs, "Use of a Multi-Axis Robotic Testing Platform to Investigate the Sagittal Mechanics of the Multi-Body Lumbar Spine," Master of Science, Department of Orthopaedic Surgery and Biomedical Engineering, The University of Tennessee Health Science Center, 54 pages (2014).
Tosteson et al., "The Cost Effectiveness of Surgical versus Non-Operative Treatment for Lumbar Disc Herniation over Two Years: Evidence from the Spine Patient Outcomes Research Trial (SPORT)," Author manuscript, pp. 1-19, published in final edited form as: Spine, vol. 33, p. 21 OS-2115 (2008).
Andersson, "Epidemiologic features of chronic low-back pain," The Lancet, vol. 354, pp. 581-585 (1999).
Aubin et al. "Variability of Strap Tension in Brace Treatment for Adolescent Idiopathic Scoliosis," Spine, vol. 24, No. 4, pp. 349-354 (1999).
Bateman, "Design, Validation, and Clinical Testing of a Novel Fastening Device for a Scoliosis Brace," Master's Thesis, UTHSC ET/D Library, pp. 1-67 (2017).
Bible et al., "Normal functional range of motion of the lumbar spine during 15 activities of daily living," J Spinal Disord Tech, vol. 23, No. 2, pp. 106-112 (2010).
Brox, "Randomized clinical trial of lumbar instrumented fusion and cognitive intervention and exercises in patients with chronic low back pain and disc degeneration," Spine, vol. 28, No. 17, pp. 1913-1921 (2003).
Cannon et al., "Evidence on the Ability of a Pneumatic Decompression Belt to Restore Spinal Height Following an Acute Bout of Exercise," JMPT, vol. 39, No. 4, pp. 304-310 (2016).
Chung et al. "A mechanical analog thoracolumbar spine model for the evaluation of scoliosis bracing technology," Journal of Rehabilitation and Assistive Technologies Engineering, vol. 5, pp. 1-9 (2018).
Chung, "Scoliosis Analog Model for the Evaluation of Bracing Technology," Theses and Dissertations (ETD), Paper 445, pp. 1-94 (2015).
Crisco, "Optimal marker placement for calculating the instantaneous center of rotation," J Biomech, vol. 27, No. 9, pp. 1183-1187 (1994).
Cuesta-Vargas et al., "Deep water running and general practice in primary care for non-specific low back pain versus general practice alone: randomized controlled trial," Clin Rheumatol, vol. 31, pp. 1073-1078 (2012).
Deyo, "Low back pain," N Engl J Med, vol. 344, No. 5, pp. 363-370 (2001).
ExMS-1, the Electromechanically-Activated Spinal Brace (Exo Dynamics, LLC, MI, USA), 10 pages, product page dated 2020, retrieved online Jun. 17, 2021.
Fritz, "Physical therapy for acute low back pain: associations with subsequent healthcare costs," Spine, vol. 33, No. 16, pp. 1800-1805 (2008).
Gilad, "A study of vertebra and disc geometric relations of the human cervical and lumbar spine," Spine, vol. 11, No. 2, pp. 154-157 (1986).
Katz et al. "Brace wear control of curve progression in adolescent idiopathic scoliosis," The Journal of Bone & Joint Surgery, vol. 92(6), pp. 1343-1352 (2010).
Kelly, "A Multiaxis Programmable Robot for the Study of Multibody Spine Biomechanics Using a Real-Time Trajectory Path Modification Force and Displacement Control Strategy," J Med Devices, vol. 7, pp. 1-7 (2013).
Krag et al., "Comparison of three lumbar orthoses using motion assessment during task performance," Spine, vol. 28, No. 20, pp. 2359-2367 (2003).
Lantz et al., "Lumbar spine orthosis wearing: I. Restriction of gross body motions," Spine, vol. 11, No. 8, pp. 834-837 (1986).
Lou et al. "An objective measurement of brace usage for the treatment of adolescent idiopathic scoliosis," Med Eng Phys., 33(3), pp. 290-294 (2011).
Loukos et al., "Analysis of the corrective forces exerted by a dynamic derotation brace (DDB)," Prosthet Orthot Int., vol. 35(4), pp. 365-372 (2011).
Medical Coverage Policy, "Thoracic Lumbosacral Orthosis with Pneumatics," Blue Cross Blue Shield, 2 pages (2013).
Modic et al., "Lumbar Degenerative Disk Disease," Radiology, vol. 245, No. 1, pp. 43-61 (2007).
Office Action corresponding to U.S. Appl. No. 16/464,833 dated Jun. 24, 2021.
Osprey Isoform Hipbelt (Osprey Packs, Inc., Cortez, CO, USA), 6 pages, retrieved online Jun. 17, 2021.
Pham et al. "Study of the pressures applied by a Cheneau brace for correction of adolescent idiopathic scoliosis," Prosthet Orthot Int., vol. 32(3), pp. 345-355 (2008).
S.P.I.N.E. Brace (Cybertech Medical/ottobock), instruction manual, 8 pages (2018).
The Aspen LSO (Aspen Medical Products, CA, USA), brochure, 2 pages (2019).
The Cybertech Orthosis (Biocybernetics International, CA, USA), product webpage, 3 pages, retrieved online Jun. 17, 2021.
The Orthotrac Pneumatic Vest (Orthofix, Inc., TX, USA), instruction manual, 6 pages (2003).
The QuikDraw Brace (Aspen Medical Products, CA, USA), brochure, 2 pages (2019).
The Vertetrac Ambulatory Traction System (Meditrac Ltd, TX, USA), brochure, 2 pages, n/d.
Wong et al. "The effect of rigid versus flexible spinal orthosis on the clinical efficacy and acceptance of the patients with adolescent idiopathic scoliosis," Spine, 33(12), pp. 1360-1365 (2008a).
Wong et al. "The effect of rigid versus flexible spinal orthosis on the gait pattern of patients with adolescent idiopathic scoliosis," Gait & Posture, vol. 27, pp. 189-195 (2008b).

\* cited by examiner

DISTRACTIVE AND MOBILITY-ENABLING LUMBAR SPINAL ORTHOSIS DEVICES, SYSTEMS, AND METHODS FOR TREATING MECHANICAL LOW BACK PAIN

RELATED APPLICATIONS

The presently disclosed subject matter claims priority to and the PCT International Application Serial No. PCT/US18/026248, filed Apr. 5, 2018, which claim priority to and the benefit of U.S. Provisional Patent Application Ser. No. 62/481,742, filed Apr. 5, 2017; the disclosure of which is incorporated herein by reference in its entirety.

TECHNICAL FIELD

The subject matter disclosed herein relates generally to orthotic devices. More particularly, the subject matter disclosed herein relates to orthotic devices, systems, and methods configured to support lumbar spine.

BACKGROUND

Lumbar spinal orthoses (LSOs) are often used as non-surgical treatment and serve to support the spine and alleviate low back pain. LSOs have also been used to treat other spinal diseases where the role of the brace is to replace the lost mechanical function brought on by the disease and provide varying amounts and combinations of immobilization, support-stabilization, or spinal decompression. More recently, dynamic LSOs have been developed to provide relief from pinched nerves or disc or spinal cord compression. These devices claim to axially decompress the spine but lack clinical or experimental evidence to support their efficacy.

Although many different orthoses exist for treating lower back problems, none of the current solutions provide the benefits of therapeutic exercise or enable independent living and return to active work. Such a device would well serve individuals suffering from disc degeneration, recovering from an injury, limited by weakness, and the elderly with several degenerative conditions. Currently, there is an unserved population of people that suffer from mechanical low back pain conditions (e.g., radiculopathy, degenerative disc disease, lumbar foraminal stenosis) that would benefit from spinal decompression and mobility.

Accordingly, it would be desirable for a lumbar spinal orthosis to be developed that offers spinal decompression while enabling some mobility to allow the user to engage in many daily living activities.

SUMMARY

In accordance with this disclosure, orthotic devices, systems, and methods configured to support a lumbar spine are provided. In one aspect, a lumbar spinal orthosis system includes a torso belt configured to be secured about a torso of a user, a pelvic belt configured to be secured about a pelvis of the user, and a distractive force mechanism connected between the torso belt and the pelvic belt. The distractive force mechanism is configured to generate a force between the torso belt and the pelvic belt acting bi-directionally across a lumbar spine of the user to substantially offload bodyweight of the user passing through the lumbar spine.

In another aspect, a method for offloading at least a portion of a user's bodyweight at a lumbar spine of the user includes securing a torso belt about a torso of the user, securing a pelvic belt about a pelvis of the user, connecting a distractive force mechanism between the torso belt and the pelvic belt, and generating a force by the distractive force mechanism between the torso belt and the pelvic belt acting bi-directionally across the lumbar spine of the user to substantially offload bodyweight of the user passing through the lumbar spine.

Although some of the aspects of the subject matter disclosed herein have been stated hereinabove, and which are achieved in whole or in part by the presently disclosed subject matter, other aspects will become evident as the description proceeds when taken in connection with the accompanying drawings as best described hereinbelow.

The features and advantages of the present subject matter will be more readily understood from the following detailed description which should be read in conjunction with the accompanying drawings that are given merely by way of explanatory and non-limiting example.

BRIEF DESCRIPTION OF THE DRAWINGS

The features and advantages of the present subject matter will be more readily understood from the following detailed description which should be read in conjunction with the accompanying drawings that are given merely by way of explanatory and non-limiting example, and in which.

DETAILED DESCRIPTION

The present subject matter provides lumbar spinal orthosis devices, systems, and methods. In particular, the present subject matter provides a back orthosis that offers spinal decompression while enabling some mobility to allow the user to engage in many daily living activities. In some embodiments, the present devices, systems, and methods offer a conservative treatment solution for mechanical low back pain by providing spinal distraction and mobility in order to sustain spinal off-loading throughout extended ranges of flexion and extension with minimal buildup of the sagittal bending moment.

Figure 1A:
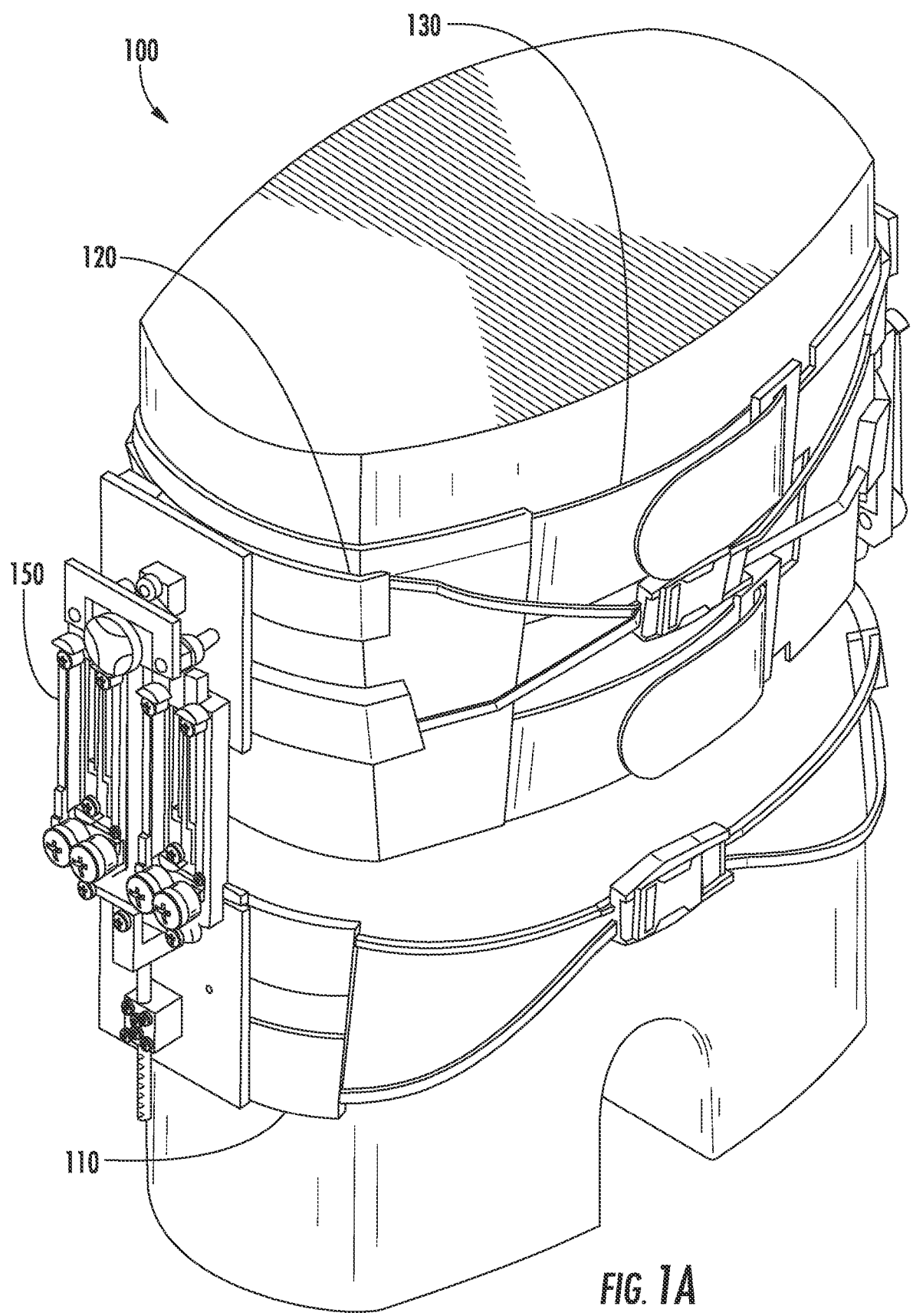
FIGS. 1A and 1B are a perspective and front view, respectively, of a distractive mobility-enabling orthosis according to an embodiment of the presently disclosed subject matter.
Figure 1B:
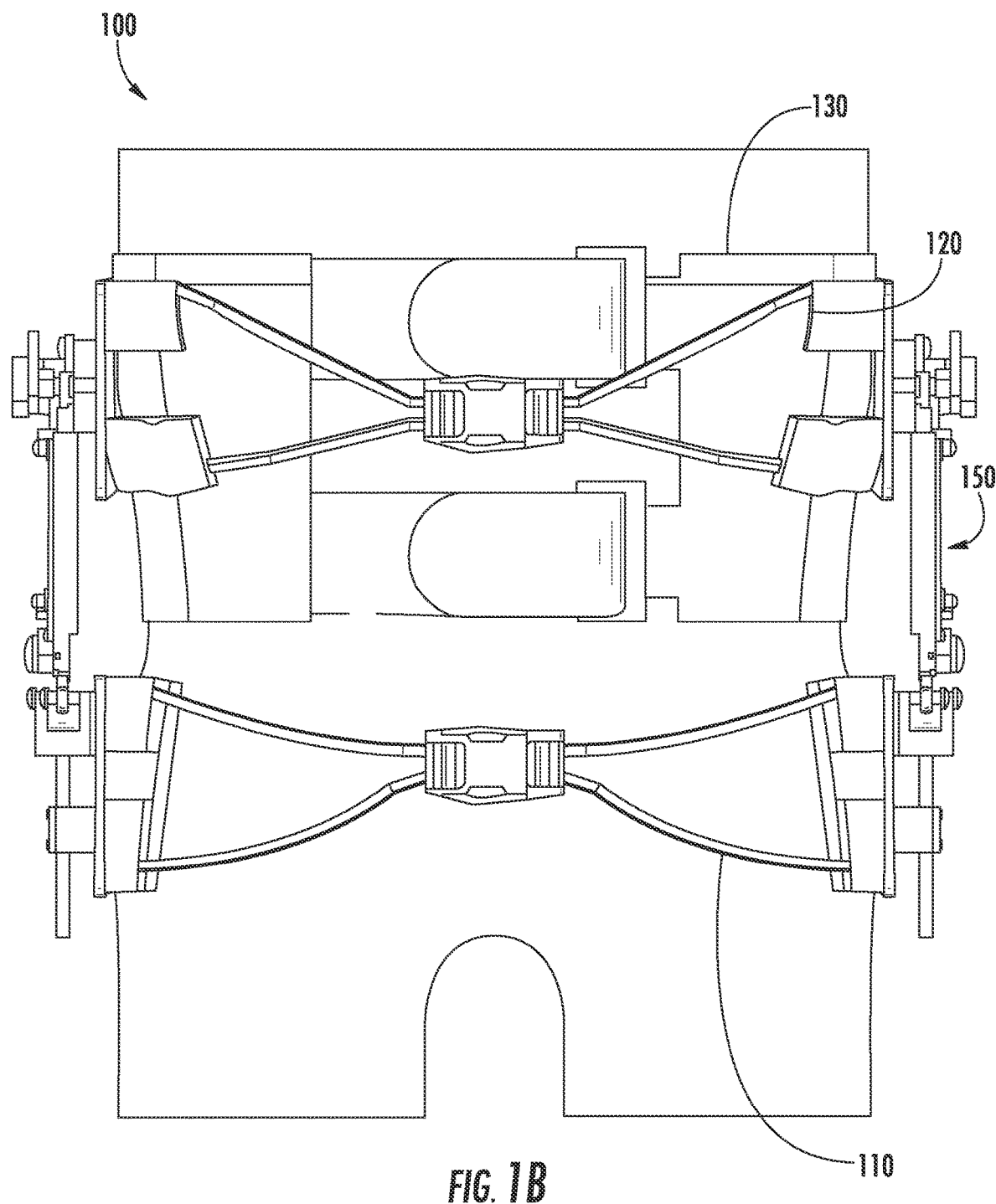
Figure 2:
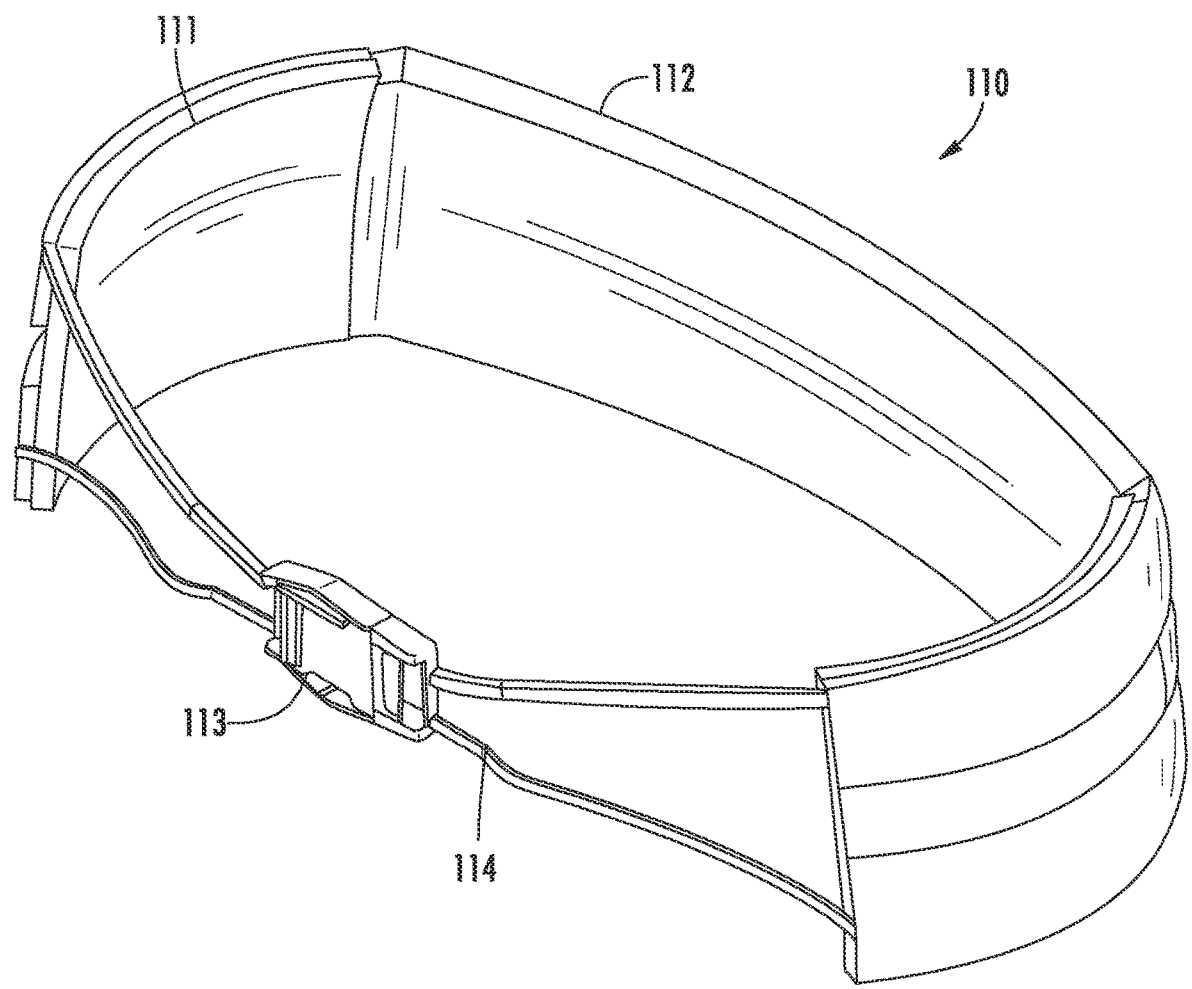
FIG. 2 is a perspective view of a pelvic belt of a distractive mobility-enabling orthosis according to an embodiment of the presently disclosed subject matter.

In one aspect, a distractive mobility-enabling orthosis, generally designated 100, is shown in FIGS. 1A and 1B. In the illustrated embodiment, the distractive mobility-enabling orthosis 100 includes one or more distractive force mechanism 150. In some embodiments, distractive force mechanism 150 is positioned on each of the left and right lateral sides of distractive mobility-enabling orthosis 100 and is operable to support at least a portion of the load exerted between the wearer's torso and hips. To support this load between the wearer's torso and hips, distractive force mechanism 150 is coupled at one end to a pelvic belt 110 that is configured to engage around the wearer's hips and conform to the wearer's natural anatomical profile and at another end to a torso belt 120 that is configured to engage the wearer's torso by wrapping around the body and conforming to the wearer's natural anatomical profile. Distractive force mechanism 150 is configured to generate a force between torso belt 120 and pelvic belt 110 acting bi-directionally across a lumbar spine of the user to substantially offload bodyweight of the user passing through the lumbar spine Referring to FIG. 2, pelvic belt 110 has a configuration that is utilized to engage around the wearer's hips and conform to the wearer's natural anatomical profile. In some embodiments, an iliac pad 111 is located on the left and right interior lateral sides of pelvic belt 110 to provide comfortable, secure engagement to the wearer's iliac crest. In some embodiments, pelvic belt 110 further includes a first moldable portion 112 that is configured to conform to the pelvis of the user. In some embodiments, first moldable portion 112 comprises thermal moldable foam, such as ethylene vinyl acetate, which can be thermally molded to the wearer's anatomy by placing it inside an oven heated to a sufficient temperature, such as approximately 200° F. or higher, for a period of time, such as ten minutes. After heating, one may wrap pelvic belt 110 around the hips until cooled to ensure that pelvic belt 110 can be contoured to the specific anatomy of the wearer. In some embodiments, pelvic belt 110 can be secured to the wearer by a first buckle 113 and a plurality of pelvic straps 114, which can be adjustable to allow for pelvic belt 110 to be tightened or loosened as desired when secured to the wearer. In the illustrated embodiment, for example, pelvic belt 110 is secured using four pelvic straps 114, which comprise Dacron or a similar material, that are coupled ventrally on the wearer using first buckle 113. When pelvic straps 114 are tightened, both the upper and lower sections of pelvic belt 110 can become more secured to the wearer simultaneously. First buckle 113 allows for the wearer to easily don and doff pelvic belt 110. In some embodiments, the configuration for pelvic belt 110 can include features that are substantially similar to those of the Osprey Isoform Men's Hipbelt (Osprey Packs, Inc., Cortez, CO, USA).

Figure 3:
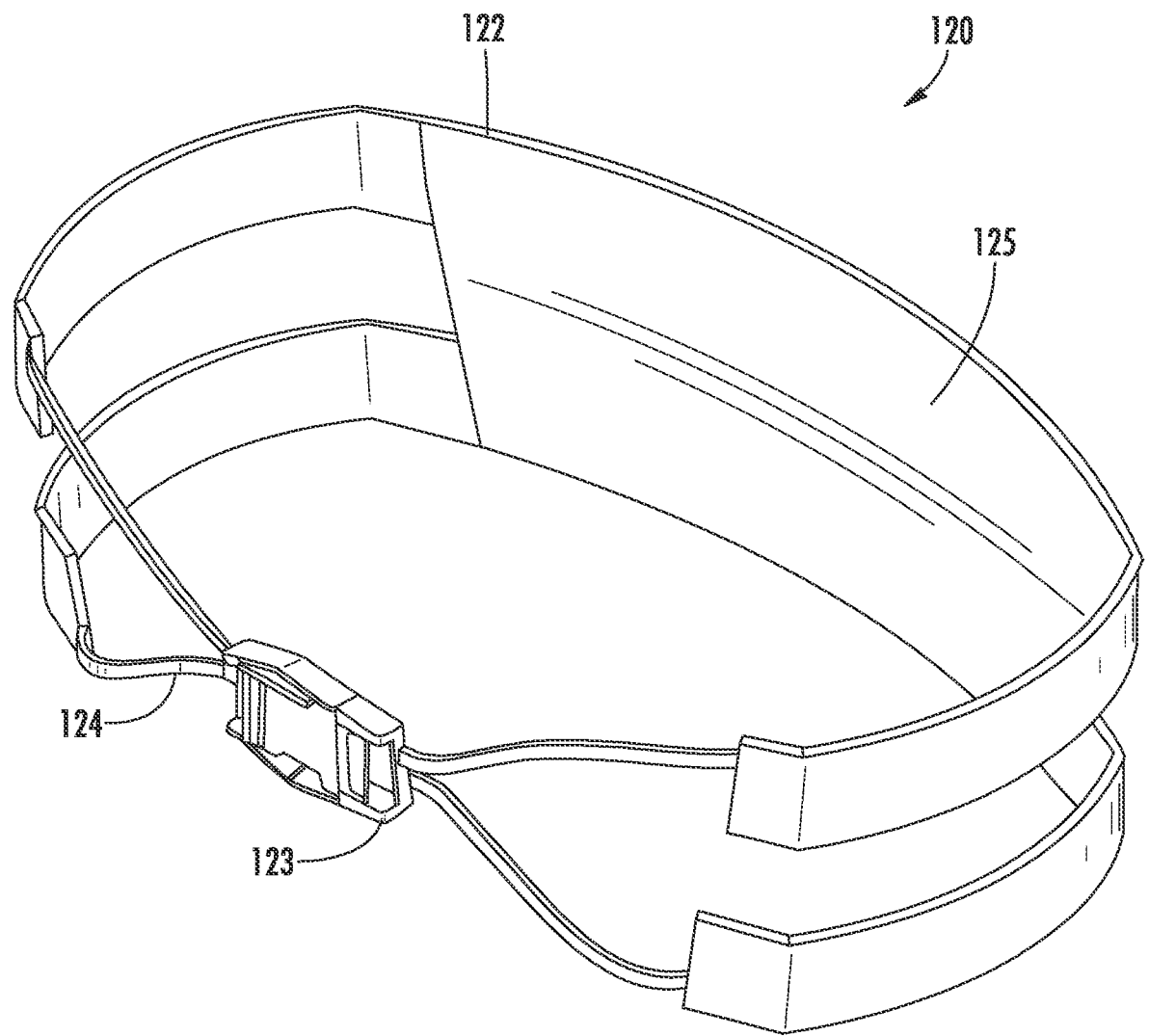
FIG. 3 is a perspective view of a torso belt of a distractive mobility-enabling orthosis according to an embodiment of the presently disclosed subject matter.

Referring now to FIG. 3, in some embodiments, torso belt 120 similarly includes a second moldable portion 122 that is configured to conform to the torso of the user. In some embodiments, second moldable portion 122 comprises a thermal moldable foam, such as ethylene vinyl acetate, which can be molded to the wearers body in a manner substantially similar to the molding of first moldable portion 112 discussed above. In the illustrated embodiment, torso belt 120 is secured to the wearer by a second buckle 123 and a plurality of torso straps 124, such as four straps comprising Dacron, that are located ventrally on the wearer. Two of torso straps 124 can be attached to each opening end of torso belt 120 and allow for torso belt 120 to be tightened or loosened on the wearer as desired when it is secured to the wearer. In this arrangement, when torso straps 124 are tightened, both the upper and lower sections of torso belt 120 can become more secured to the wearer simultaneously. Second buckle 123 allows for the wearer to easily don and doff torso belt 120.

Figure 4:
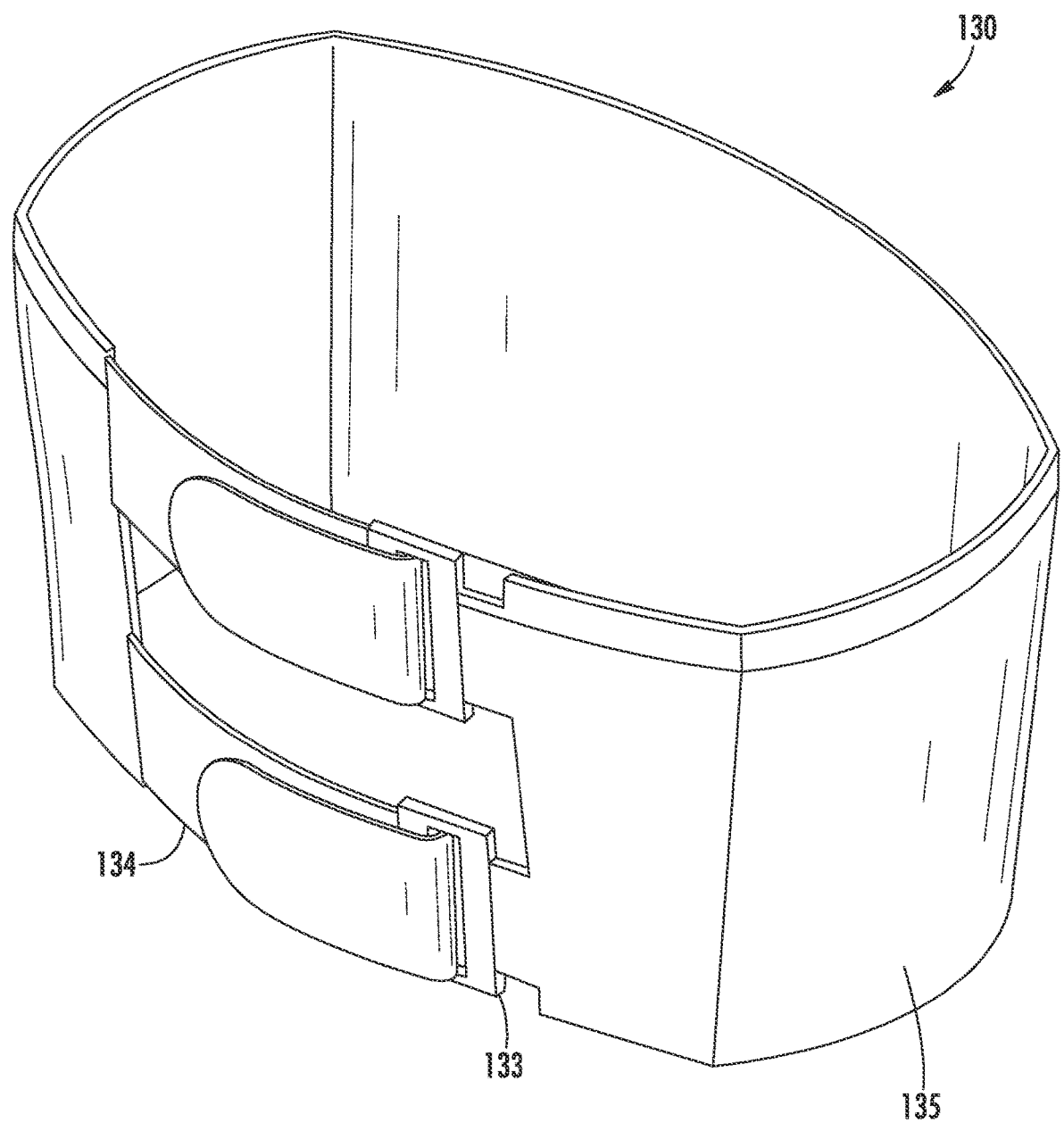
FIG. 4 is a perspective view of a torso glove for use with a torso belt of a distractive mobility-enabling orthosis according to an embodiment of the presently disclosed subject matter.

To further enhance the engagement of torso belt 120 to the wearer, in some embodiments, distractive mobility-enabling orthosis 100 includes an extra engagement component, hereinafter referred to as a torso glove 130. In such embodiments, torso glove 130 can comprise a neoprene vest, such as is illustrated in FIG. 4. An advantage of adding torso glove 130 can be that it can engage more of the wearer's surface area and prevent slippage of distractive mobility-enabling orthosis 100 on the wearer's torso. Donning and doffing of torso glove 130 can be made possible through any of a variety of securing mechanisms known to those having skill in the art. In the illustrated embodiment, for example, torso glove 130 is secured using two loops 133 and two glove straps 134 that are attached to each opening end of torso glove 130. Glove straps 134 can be configured to go through respective ones of loops 133 and then attach to itself, such as through a hook-and-loop fastener. When glove straps 134 are tightened, the material of torso glove 130 can be designed to stretch so that torso glove 130 becomes very securely engaged to the wearer's torso.

Torso belt 120 can then be configured to wrap around the wearer's torso after the wearer has donned torso glove 130. To provide a secure engagement between the elements, in some embodiments, the interior of torso belt 120 is layered with a loop material 125 of a hook-and-loop fastener (Velcro) that attaches to a corresponding hook material 135 on the exterior of torso glove 130. Those having ordinary skill in the art will recognize, however, that the coupling of torso belt 120 to torso glove 130 is not intended to be limited to particular arrangement of loop material 125 and hook material 135. Rather, any of a variety of other coupling mechanisms can be used to improve the engagement between these elements.

Figure 5:
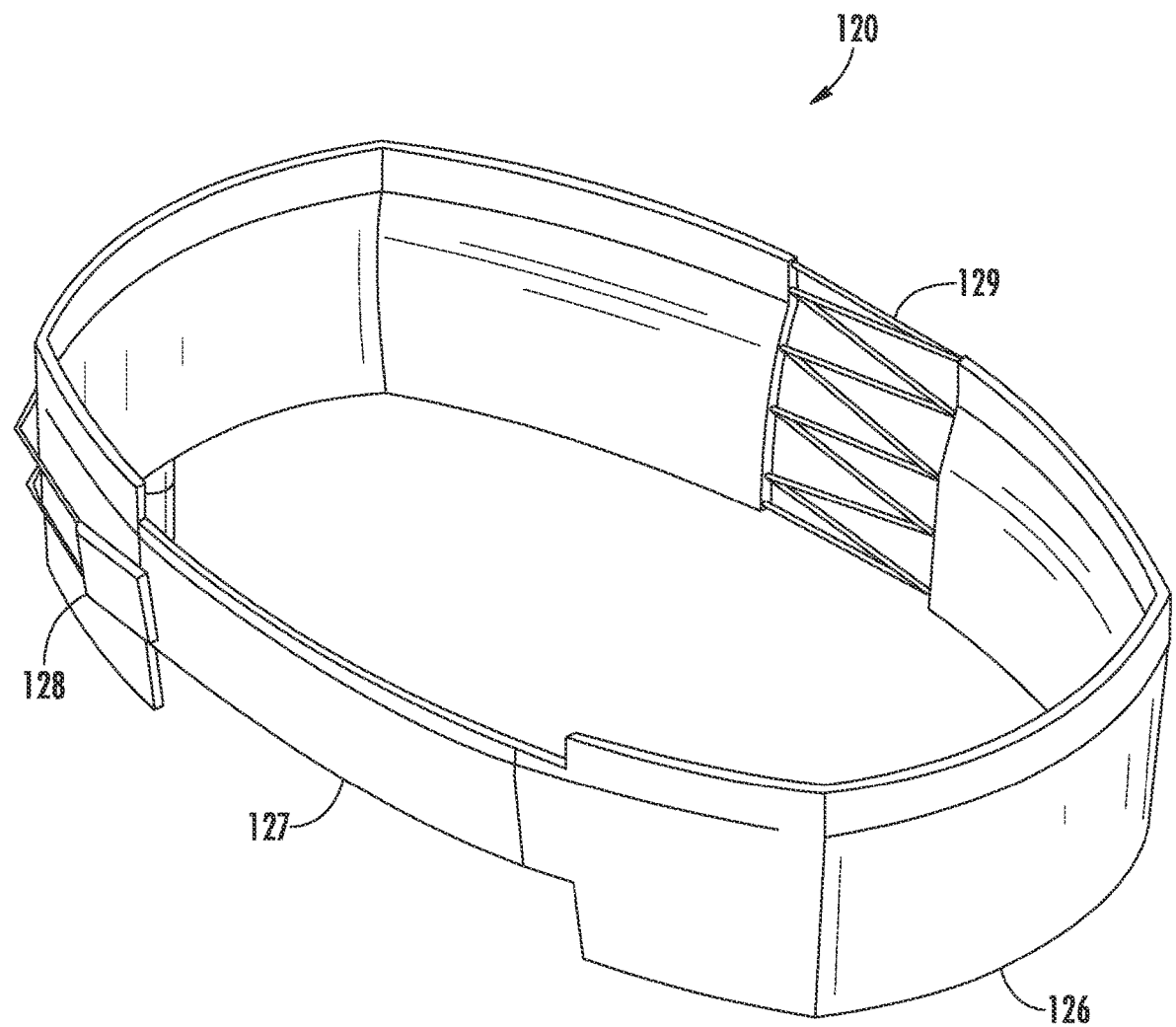
FIG. 5 is a perspective view of a torso belt of a distractive mobility-enabling orthosis according to another embodiment of the presently disclosed subject matter.

Alternatively, in another embodiment illustrated in FIG. 5, torso belt 120 includes a flexible, semi-rigid material layer 126, such as UBL, which can be wrapped around the torso. In this configuration, torso belt 120 is then secured to the user through the use of overlapping straps 127, such as complementary straps that are fastened suing a hook-and-loop closure, that are located ventrally on the wearer. The fit of torso belt 120 can be adjusted by pulling on a pull tab 128 associated with a cinching mechanism 129 located dorsally on the wearer. This configuration for torso belt 120 can include features that are substantially similar to those of the S.P.I.N.E. Brace (Cybertech Medical/ottobock).

Regardless of the particular configuration of each of the elements, distractive mobility-enabling orthosis 100 provides an effective body engagement mechanism. In particular, distractive mobility-enabling orthosis 100 can be designed such that pelvic belt 110 remains secured to the iliac crest, and torso belt 120—either with or without torso glove 130—remains secured to the wearer's torso during their daily life activities. In addition, distractive mobility-enabling orthosis 100 can be adapted for patients of any of a range of different sizes.

As discussed above, the mechanism by which a distractive force can be applied to the wearer of distractive mobility-enabling orthosis 100 is referred to as distractive force mechanism 150. In some embodiments, this mechanism is placed on the left and right sides of the wearer and connects the superior engagement components of distractive mobility-enabling orthosis 100 (e.g., to torso belt 120) with the inferior engagement components (e.g., with pelvic belt 110). In this arrangement, distractive force mechanism 150 can provide a downward force on the iliac crest through the engagement of pelvic belt 110 and an upward force to the wearer's torso through the engagement of torso belt 120. In some embodiments, for example, distractive mobility-enabling orthosis 100 can be designed to support all or a percentage of the torso weight of an average male individual (e.g., half of about 170 lbs. (756 N), assuming his or her torso weight is 40% of the total body weight), with this force being applied and maintained throughout extended ranges of motion. This design parameter can define an upper limit for the force that needs to be supported, which equates to about 300 N.

This distractive force can be provided in any of a variety of forms for distractive force mechanism 150. For example, in a first embodiment illustrated in FIGS. 6 through 12, distractive force mechanism 150 include a pelvic belt assembly 151 that is configured to be securely engaged to pelvic belt 110, such as by using an arrangement of straps and/or fasteners, a torso belt assembly 152 that is likewise configured to be securely engaged to torso belt 120, and a plurality of mechanical actuators 153 that are coupled therebetween.

Figure 7:
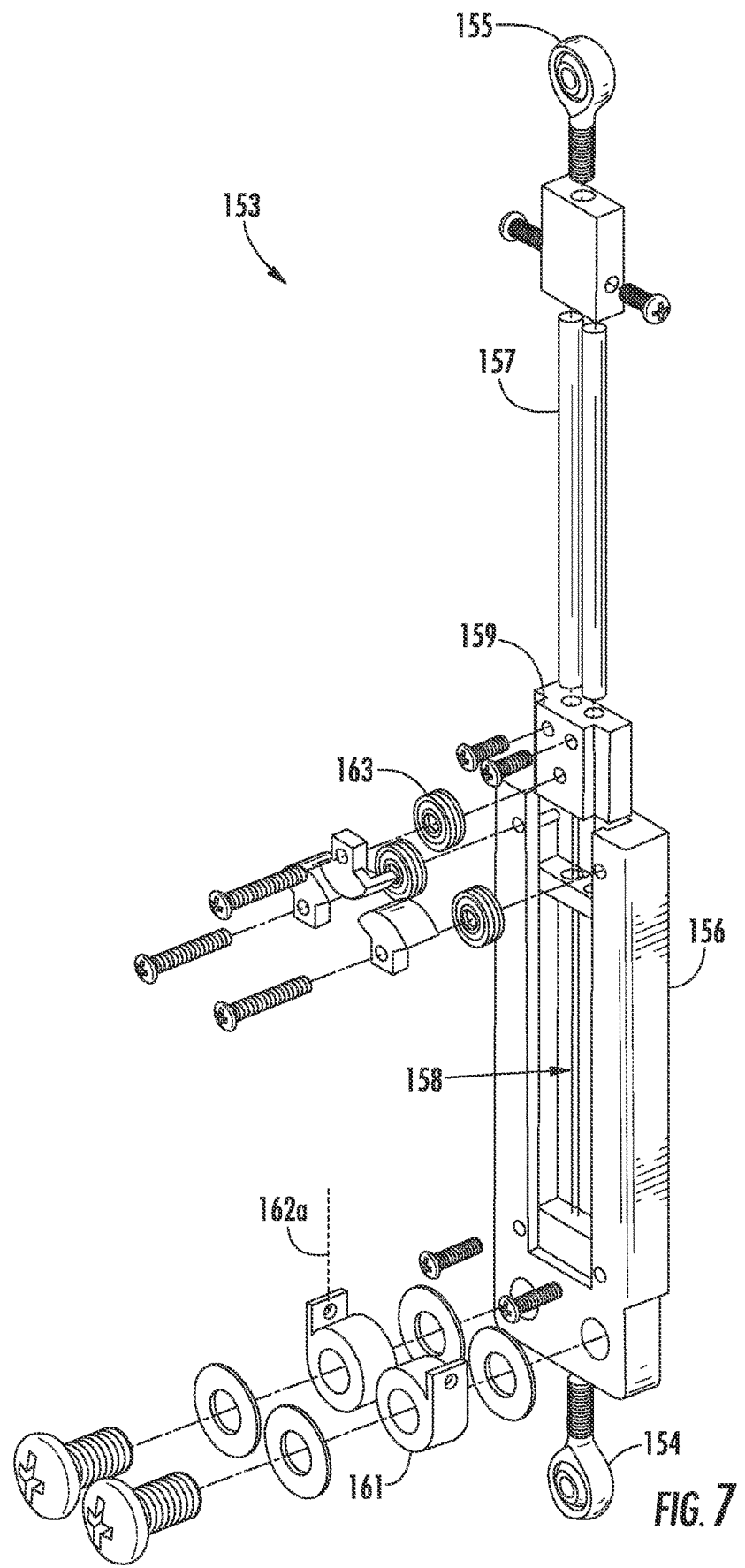
FIG. 7 is a perspective exploded view of a mechanical actuator of a distractive force mechanism a perspective view of a torso belt of a distractive mobility-enabling orthosis according to an embodiment of the presently disclosed subject matter.

Each of mechanical actuators 153, the components of which are illustrated in FIG. 7, can be pivotably attached inferiorly to pelvic belt assembly 151, such as via first tie rod end 154, and superiorly to torso belt assembly 152, such as via a second tie rod end 155. In some embodiments, a housing 156 is connected to first tie rod end 154, and one or more rods 157 (e.g., aluminum rods) are connected to second tie rod end 155, wherein rods 157 are configured to be slidable within a channel 158 formed within housing 156. In some embodiments, for example, channel 158 has a substantially c-shaped cross section, and an end of rods 157 are connected to a channel slot nut 159 that is configured to be slidably retained within channel 158.

To establish the distractive force between pelvic belt 110 and torso belt 120, a cable tensioning system 160 couples housing 156 and rods 157 together. In the embodiment illustrated in FIGS. 6 through 12, cable tensioning system 160 includes one or more biasing elements 161 associated with each of mechanical actuators 153. In some embodiments, for example, each of biasing elements 161 is a constant force spring that is positioned within housing 156 of a respective one of mechanical actuators 153. Unlike conical springs that have constant rate of force per unit length of spring deformation, a constant force spring exerts a specific force through the entire range of motion of the spring. In some embodiments, the springs of biasing elements 161 are laminated or stacked to provide an increased force output without substantially changing the size. In some embodiments, such springs are held in housings, such as by pinned connectors and ball bearings or by being enclosed in a cavity.

In any configuration, biasing elements 161 are each connected to a first end of a cable 162 of cable tensioning system 160, and a second end of cable 162 is connected to torso belt assembly 152 by way of rods 158. In some embodiments, cable 162 includes a first cable portion 162*a* that is routed from one of biasing elements 161 through one or more first pulley assembly 163 mounted to housing 156, such as to a superior end of housing 156, to a connector 164. A second cable portion 162*b* is also connected to connector 164 and is routed through one or more second pulley assembly 165 mounted to rods 157, such as to channel slot nut 159, to torso belt assembly 152.

Figure 8:
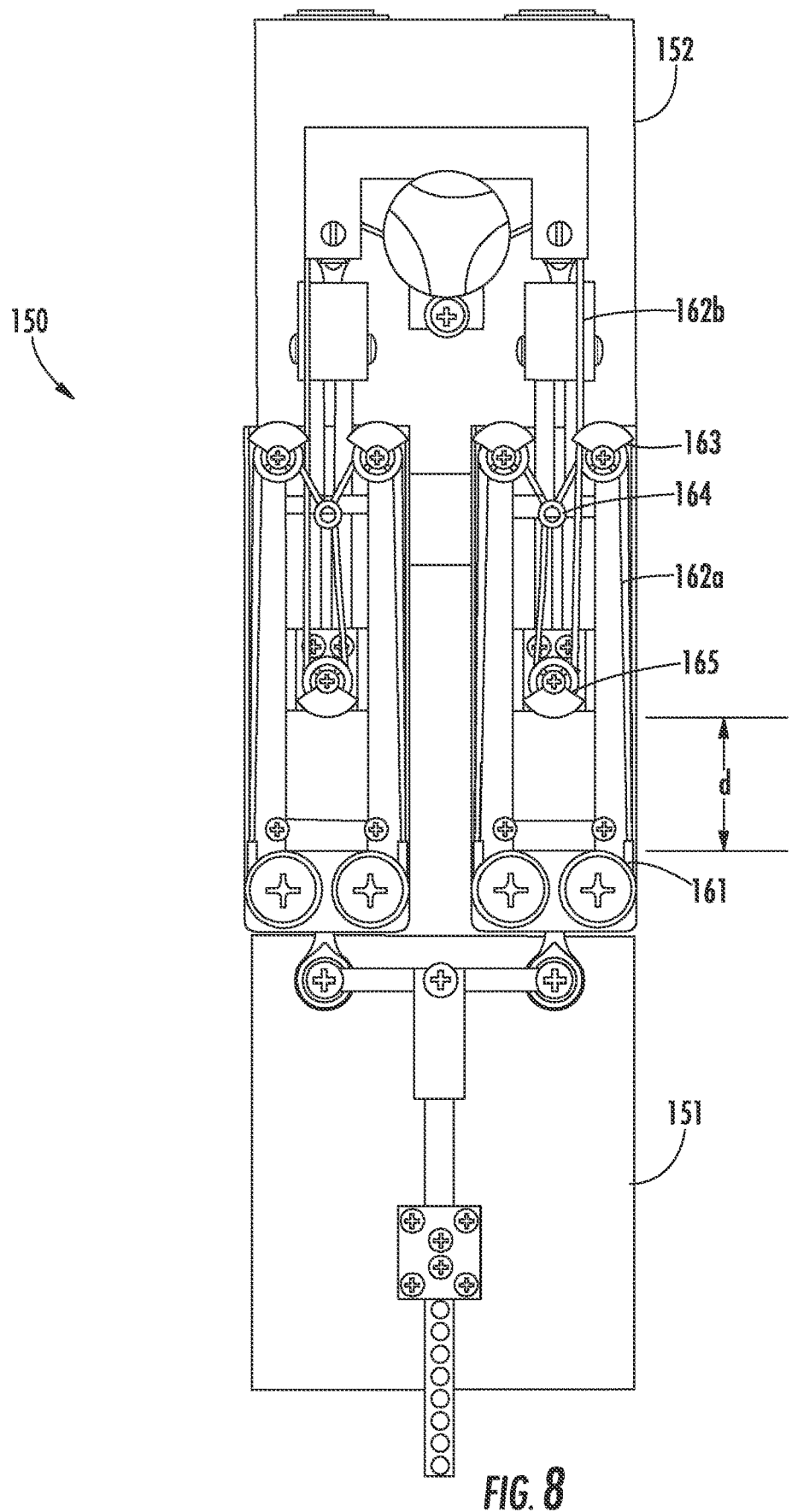
FIG. 8 is a front view of a distractive force mechanism of a distractive mobility-enabling orthosis in a loaded state according to an embodiment of the presently disclosed subject matter.

In this configuration, when torso belt assembly 152 travels vertically with respect to pelvic belt assembly 151 to a point at which a force resistance is met that is equal to or greater than the total force resistance of all of biasing elements 161, biasing elements 161 can be extended such that rods 157 move a distance d relative to housing 156, and connector 164 that connects first cable portion 162*a* and second cable portion 162*b* travels downward, such as is shown in FIG. 8. As a result, when distractive force mechanism 150 is engaged in this way, a downward force can be transmitted to pelvic belt 110 through first tie rod end 154 of each of mechanical actuators 153, and an upward force can be transmitted to the wearer through torso belt 120. In addition, in embodiments in which torso glove 130 enhances the engagement of torso belt 120 to the wearer's anatomy, torso glove 130 can be thought of as a human suspension system that is essentially pulled upward on the wearer's torso as distractive force mechanism 150 lifts upward. Assuming that all of the engagement components are secured to the wearer without slipping, a distractive force can more effectively be applied to the wearer.

Figure 6:
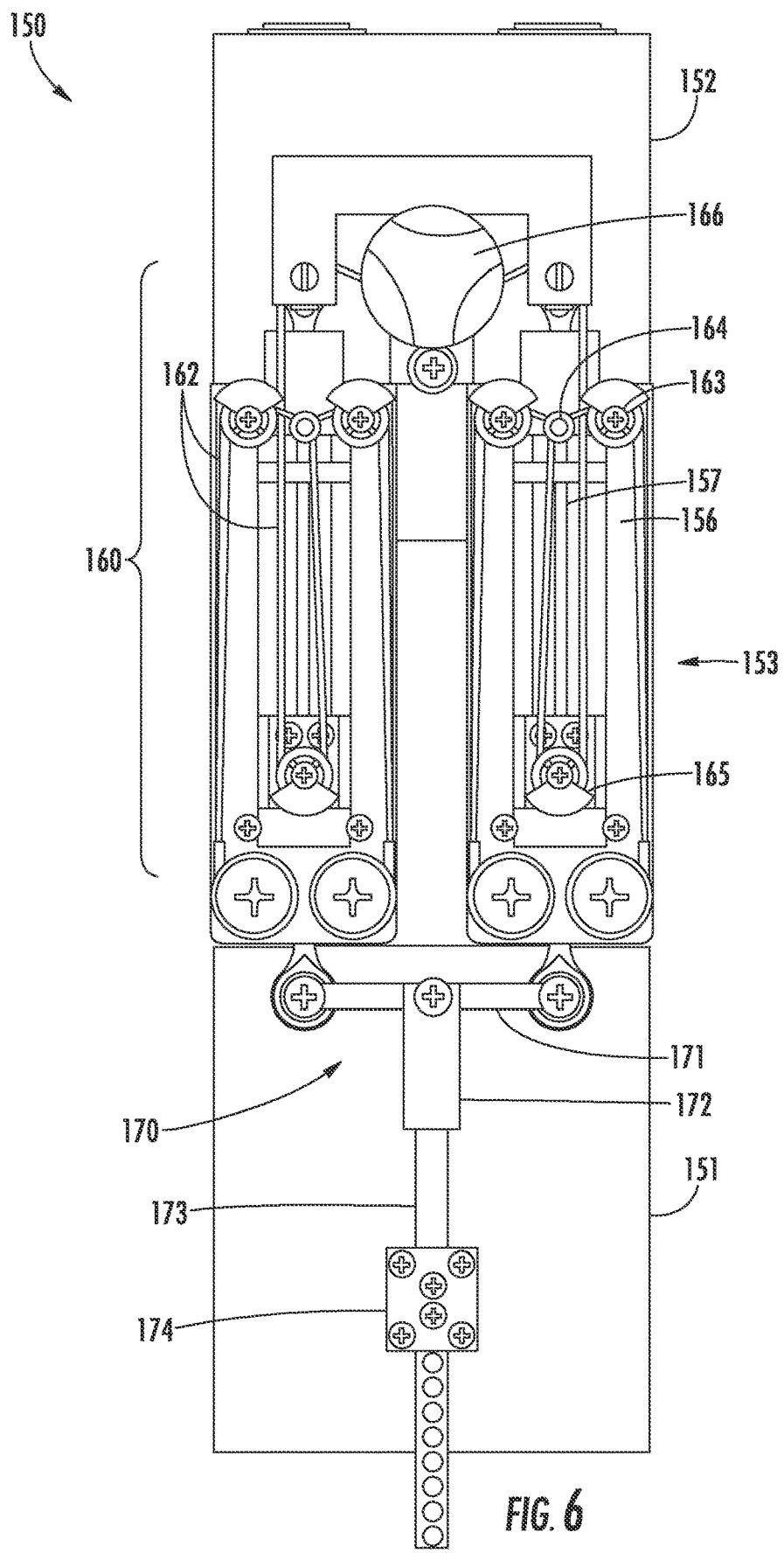
FIG. 6 is a front view of a distractive force mechanism of a distractive mobility-enabling orthosis according to an embodiment of the presently disclosed subject matter.

Although the embodiment illustrated in FIGS. 6 and 8 shows two of mechanical actuators 153 as being substantially the same height, each of mechanical actuators 153 can be configured to function essentially independently of each other, meaning that if one of mechanical actuator 153 needs to lengthen and the other shorten during movement, it is able to do so. In some embodiments, each of biasing elements 161 can be set to have a substantially equal force output, such as about five pounds each. For example, since each distractive force mechanism 150 in the configuration illustrated in FIGS. 6 though 12 has four constant force springs, the total distractive force output can be set to approximately 40 pounds (approximately 180 N). Of course, those having ordinary skill in the art will recognize that, by adjusting the number and/or force outputs of biasing elements 161, the total force output of distractive force mechanism 150 can be altered.

Figure 9:
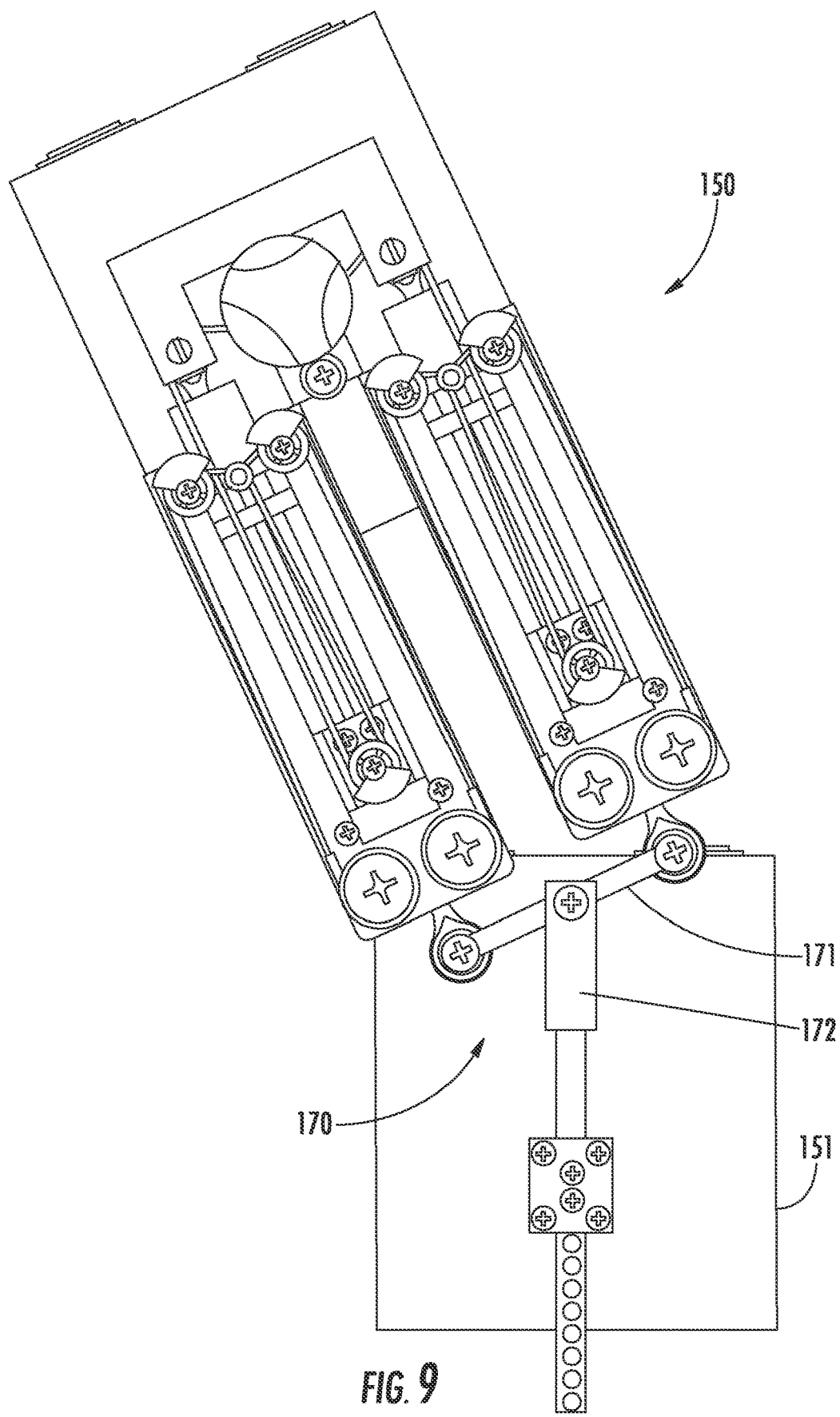
FIGS. 9 and 10 are front views of a distractive force mechanism of a distractive mobility-enabling orthosis in a state of flexion or extension according to an embodiment of the presently disclosed subject matter.
Figure 10:
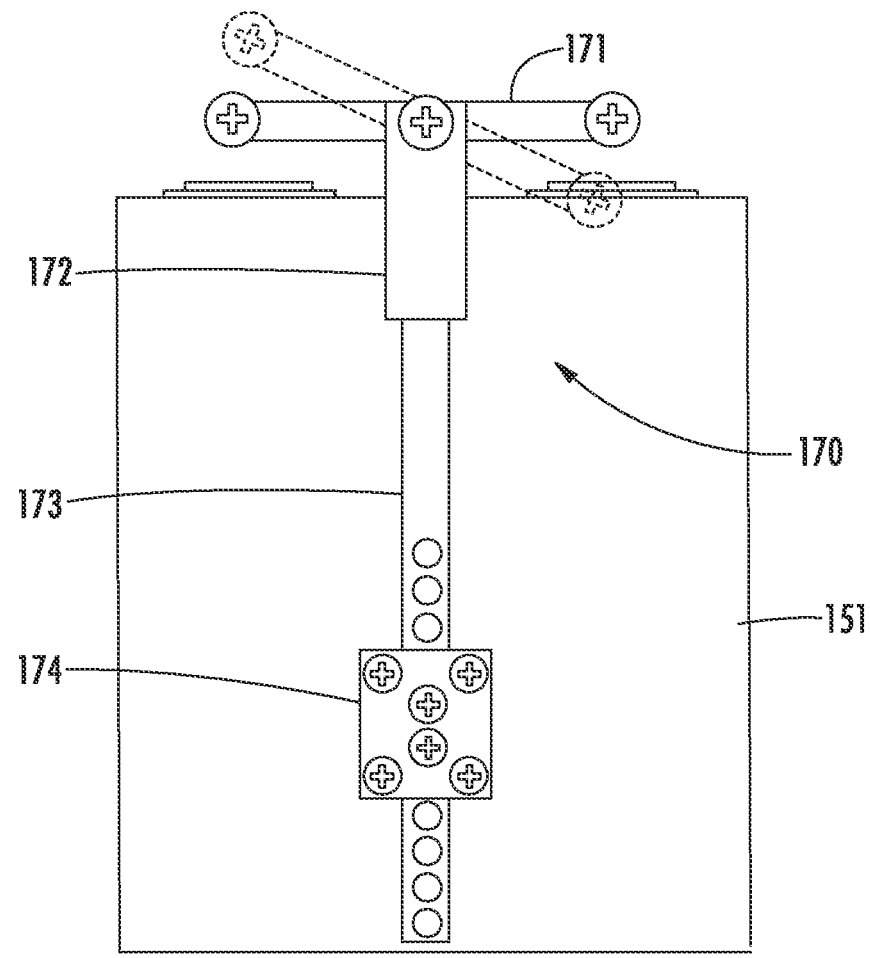

While providing this distractive force between pelvic belt assembly 151 and torso belt assembly 152, in some embodiments, distractive force mechanism 150 is further configured to allow for axial rotation and/or flexion or extension movements. In some embodiments, for example, first tie rod end 154 is connected to pelvic belt assembly 151 by a mobility enabling component 170 that allows distractive force mechanism 150 to pivot and/or twist relative to pelvic belt assembly 151. In one embodiment illustrated in FIGS. 9 and 10, first tie rod end 154 of each of mechanical actuators 153 is connected to left and right sides of a rocker 171, respectively, which is pivotably connected to a rod clevis 172 that is attached to an axis adjustment bar 173, and axis adjustment bar 173 is connected to pelvic belt assembly 151, such as by a receiver 174. In this configuration, rocker 171 is attached to rod clevis 172 at a pivotable joint that allows the user to bend freely in flexion or extension as shown in FIGS. 9 and 10 relative to its original position shown in FIG. 6.

Figure 11:
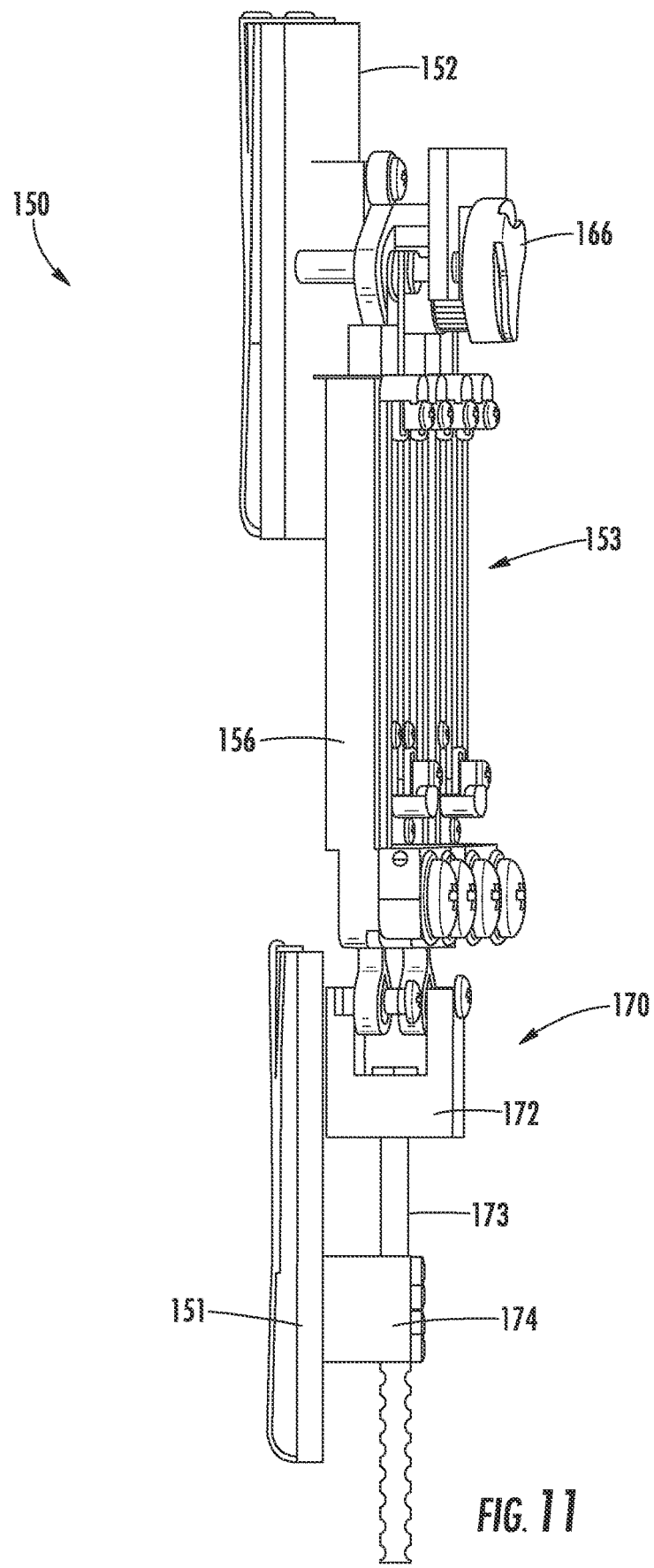
FIGS. 11 and 12 are side views of a distractive force mechanism of a distractive mobility-enabling orthosis in a state of axial rotation according to an embodiment of the presently disclosed subject matter.
Figure 12:
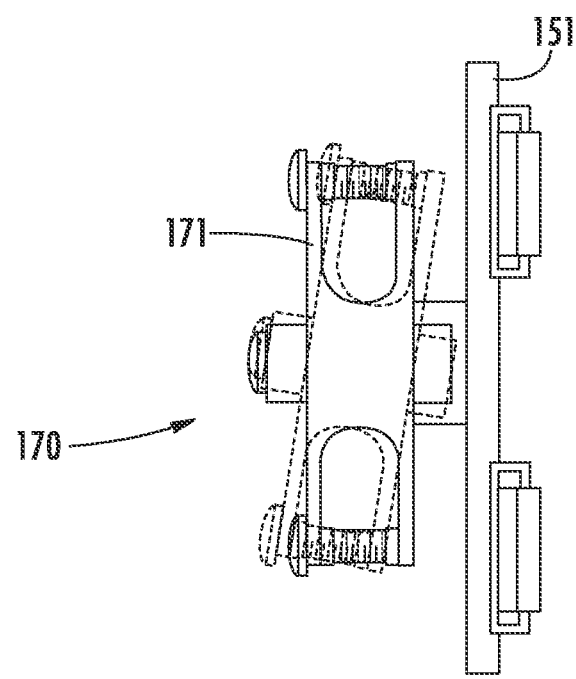

In addition, the connection to pelvic belt assembly 151 can further allow for axial rotation movements. In some embodiments, the superior end of axis adjustment bar 173 can be inserted into a hole on the superior side of rod clevis 172, and the posterior side of rod clevis 172 can securely sit on axis adjustment bar 173 with a diameter larger than the hole in the swivel. Therefore, rod clevis 172 can rotate freely about the long axis of axis adjustment bar 173 under simulated axial rotation as shown in FIGS. 11 and 12.

Although particular configurations for mobility-enabling component 170 are shown in FIGS. 9 through 12 and described above, those having ordinary skill in the art will recognize that any of a variety of other configurations for mobility-enabling component 170 can be used with the presently-disclosed subject matter. In any configuration, because distractive force mechanism 150 in the embodiments illustrated in FIGS. 6 through 12 uses biasing elements 161, such as constant force springs, to apply the input force into distractive force mechanism 150, mobility-enabling component 170 can thus be configured to allow flexion/extension or axial rotation movement without causing a significant reduction in the force output from the mechanism. Because of this, the wearer can perform daily life activities with minimal resistance to movement and with a distractive force being applied at all times by distractive mobility-enabling orthosis 100.

In addition, in some embodiments, distractive mobility-enabling orthosis 100 can include one or more adjustment mechanisms that can further tailor the operation of distractive mobility-enabling orthosis 100 to the user's preferences. For example, in some embodiments, the portion of cable 162 that is connected to tension belt assembly 152 is connected by way of a tension-adjustment mechanism 166 that is mounted to tension belt assembly 152. Tension-adjustment mechanism 166 is operable to adjust the tension within cable tensioning system 160 to thereby adjust a force applied between pelvic belt 110 and torso belt 120 by distractive force mechanism 150. In some embodiments, such a tension-adjustment mechanism 166 is a tensioning knob that is attached in the middle of torso belt assembly 152. For instance, in a loaded state, second cable portion 162b can be shortened in length when tension-adjustment mechanism 166 is manipulated, such as by turning a tensioning knob, and channel slot nut 159 can be pulled upward. In this way, where biasing element 161 comprises a constant force spring, adjustment of tension-adjustment mechanism 166 adjusts the working length of the spring over which the distractive force is applied.

In some embodiments, distractive mobility-enabling orthosis 100 further includes a mechanism to set the location of the rotational axis 200 of distractive mobility-enabling orthosis 100. In some embodiments, it can be desirable for rotational axis 200 to be approximately aligned with a center of rotation 210 of the lumbar spine, which previous work has shown to be located at around the L3-L4 intervertebral disc, as well as near the load bearing/neutral axis 211 of the lumbar spine. In the embodiment discussed above with respect to FIGS. 6 through 12, this alignment can be accomplished by positioning the axis of rotation of rocker 171 of mobility enabling component 170 at or near center of rotation 210. In some embodiments, rocker 171 can be configured to rotate about a pivot axis at its connection with rod clevis 172.

Figure 13A:
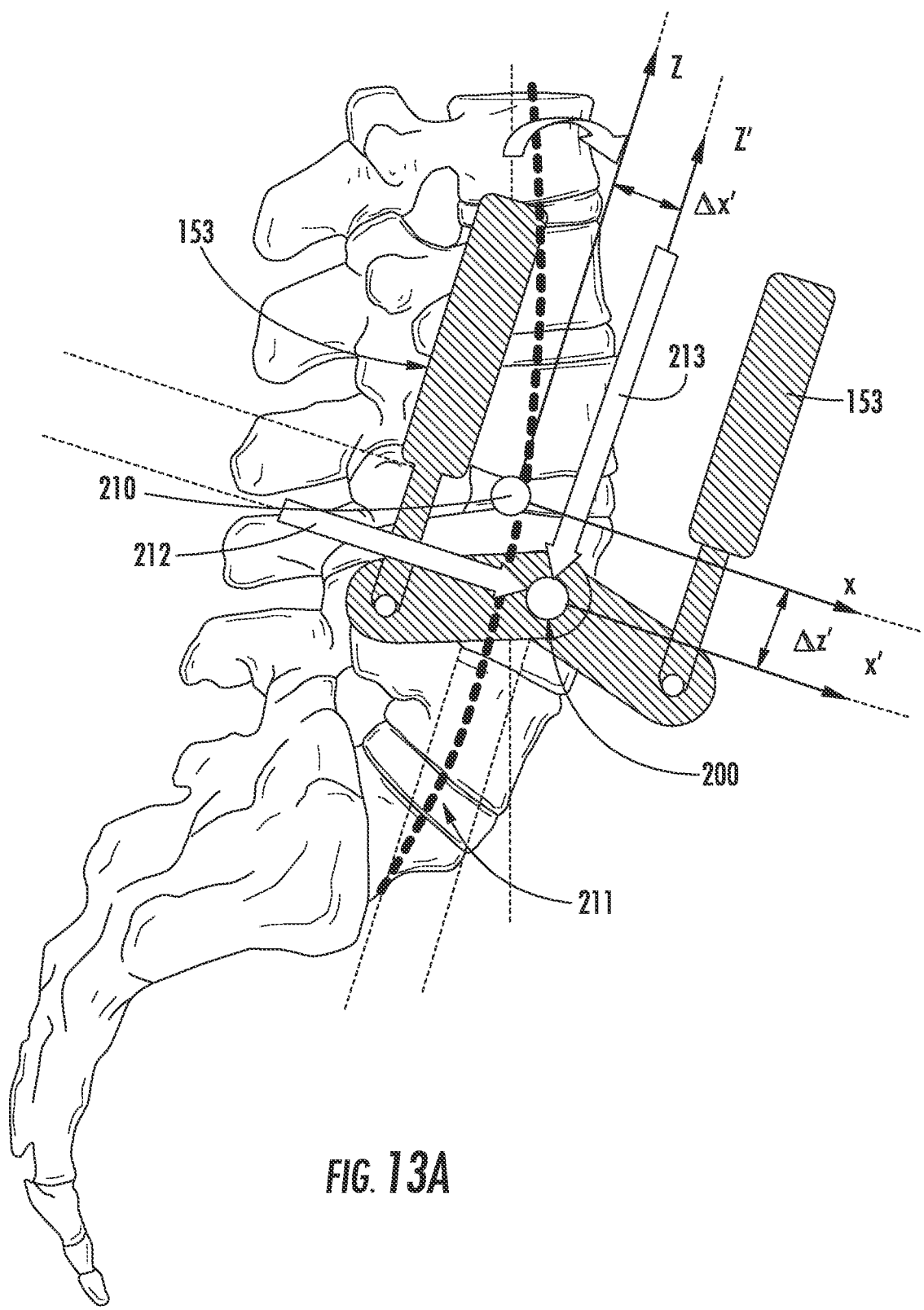
FIGS. 13A and 13B are side views illustrating positioning of a mobility enabling component of a distractive mobility-enabling orthosis relative to human spinal anatomy according to another embodiment of the presently disclosed subject matter.
Figure 13B:
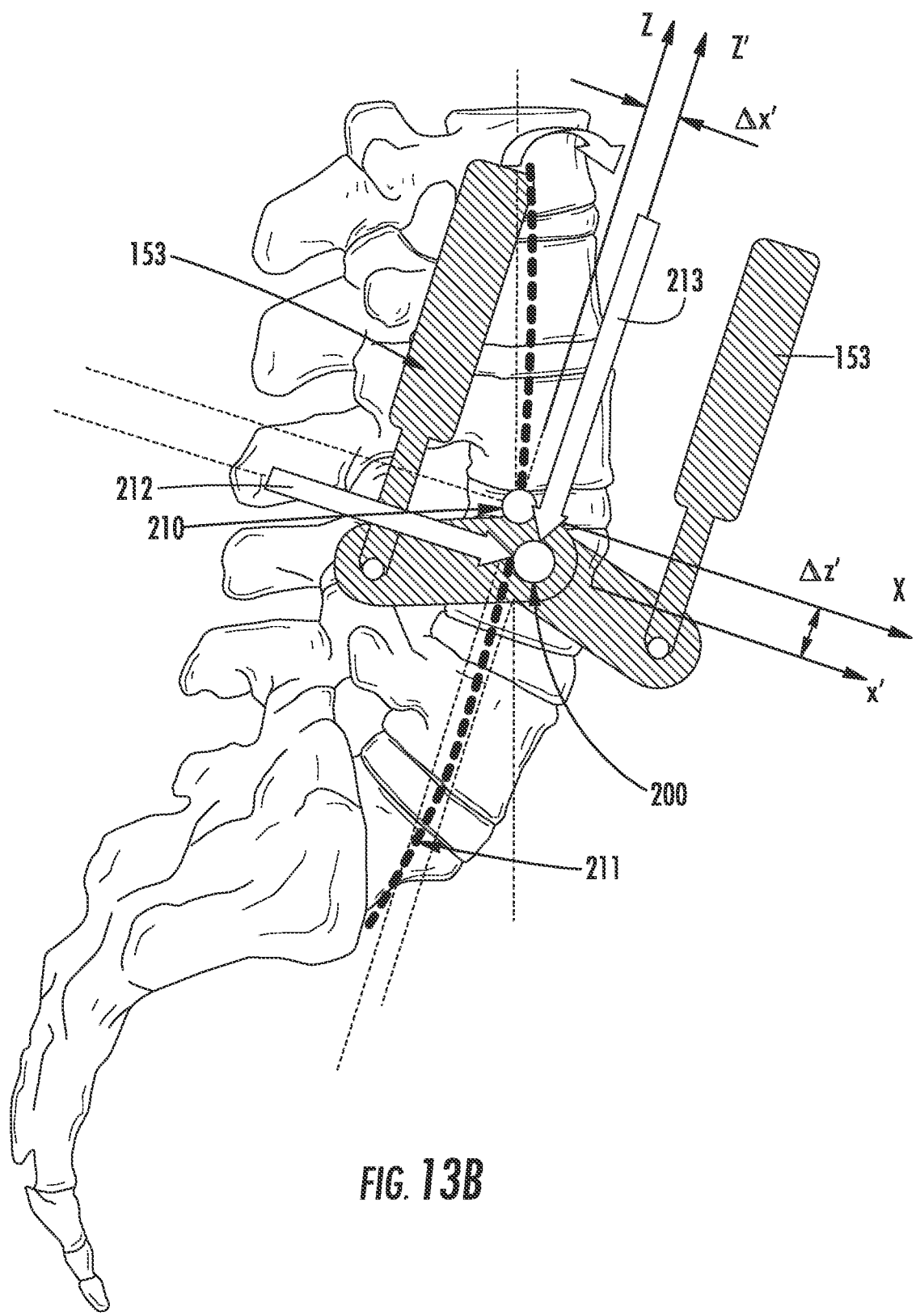

If rotational axis 200 of distractive mobility-enabling orthosis 100 is not aligned properly with center of rotation 210 of the lumbar spine as shown in FIG. 13A, the distractive force from distractive force mechanism 150 can create lateral and vertical loads 212 and 213 off-axis to center of rotation 210 of the spine ($\Delta x'$ and $\Delta z'$), which can contribute additional bending moments about the spine. By correctly aligning rotational axis 200 of distractive mobility-enabling orthosis 100 close to center of rotation 210 of the lumbar spine as shown in FIG. 13B, however, minimal additional bending moment may be required to move. Correct alignment of rotational axis 200 of distractive mobility-enabling orthosis 100 with center of rotation 210 of the lumbar spine can ensure that distractive mobility-enabling orthosis 100 and the lumbar spine work together during extended ranges of flexion and extension. In addition, in embodiments in which distractive force mechanism 150 includes multiple mechanical actuators 153, positioning mechanical actuators 153 substantially equidistant from rotational axis 200 can ensure that minimal bending moment is developed by distractive force mechanism 150.

In some embodiments, rotational axis 200 of distractive mobility-enabling orthosis 100 can be positioned vertically with respect to pelvic belt 110 by adjusting the vertical location of axis adjustment bar 173. In this regard, in some embodiments, the position of axis adjustment bar 173 relative to receiver 174 can be adjustable. Similarly, rotational axis 200 of distractive mobility-enabling orthosis 100 can be adjusted horizontally by adjusting a lateral position of torso belt assembly 152 and/or pelvic belt assembly 151 on torso belt 120 and pelvic belt 110, respectively. In this arrangement, pelvic belt assembly 151 allows for rotational axis height adjustment as well as for axial rotation and or flexion or extension movements as shown in FIGS. 10 and 12.

In any configuration, mobility enabling component 170 can allow for flexion, extension, and axial rotation movement with minimal resistance from distractive mobility-enabling orthosis 100. In some embodiments, for example, a targeted functional range of motion (ROM) of distractive mobility-enabling orthosis 100 can be about 25 degrees of flexion, 10 degrees of extension, and 10 degrees of axial rotation as most daily life activities are encompassed within this range of motion.

As a result, this embodiment of distractive mobility-enabling orthosis 100 exhibits improvements in off-loading capacity relative to a prior device described in U.S. Pat. No. 9,480,593. For example, for a 300 N upper body weight loading condition in the upright stance configuration and through extended ranges of 25° flexion and 10° of extension, the percentage of the applied load carried by each orthosis as well as the loads transferred to the spine, along with the loads carried by the orthoses and the load transferred through the lumbar spine, are given in Table 1 below:

TABLE 1

| Degrees of Rotation | Applied Load (N) | | Transferred Load (N) | | Brace Load (N) | | Brace Load as a Percentage of Applied Load (%) | |
|---|---|---|---|---|---|---|---|---|
| | '593 | DMO 100 | '593 | DMO 100 | '593 | DMO 100 | '593 | DMO 100 |
| At 10° Extension | 290 | 288 | 43 | −5 | 247 | 293 | 85 | 102 |
| At 0° | 300 | 288 | 0 | 6 | 300 | 282 | 100 | 98 |
| At 25° Flexion | 291 | 293 | 119 | 3 | 172 | 290 | 59 | 99 |

At end range flexion, the current embodiment of distractive mobility-enabling orthosis 100 supported almost the entire applied load (i.e., 99%) compared to 59% for the prior device. In addition, at the end range extension, the entire applied load was supported and the spine was placed under slight traction (102%) compared to 85% support for the prior device.

Further, the sagittal bending moment versus angular displacement response of distractive mobility-enabling orthosis 100 is improved relative to the prior device, as shown in Table 2 below:

TABLE 2

| Degrees of Rotation | Applied Moment (Nm) | | Transferred Moment (Nm) | | Brace Effect (Nm) | | Brace Effect as a Percentage of Applied Moment (%) | |
|---|---|---|---|---|---|---|---|---|
| | '593 | DMO 100 | '593 | DMO 100 | '593 | DMO 100 | '593 | DMO 100 |
| At 10° Extension | 15 | 10.9 | 0 | 6.5 | 15 | 4.4 | 100 | 40 |
| At 25° Flexion | 32.4 | 21.7 | 13.8 | 15.1 | 18.6 | 6.6 | 57 | 30 |

The applied moment required to reach 25° flexion was 21.7 Nm for distractive mobility-enabling orthosis 100 and 32.4 Nm for the prior device. A similar reduction in the bending moment was required to reach 10° of extension by distractive mobility-enabling orthosis 100 (10.9 Nm) compared to the prior device (15.0 Nm). The moment buildup of each orthosis, referred to as the brace effect, is also listed in Table 2. At end range flexion, only 6.6 Nm of sagittal moment was required for distractive mobility-enabling orthosis 100 compared to 18.6 Nm for the prior device. At end range extension, the brace effect of distractive mobility-enabling orthosis 100 was 4.4 Nm compared to 15.0 Nm for the prior device. The moment buildup for distractive mobility-enabling orthosis 100 was 27% less than that of the prior device (i.e., 30% compared 57%) at end range flexion and 60% less at end range extension (i.e. 40% compared to 100%).

Figure 14:
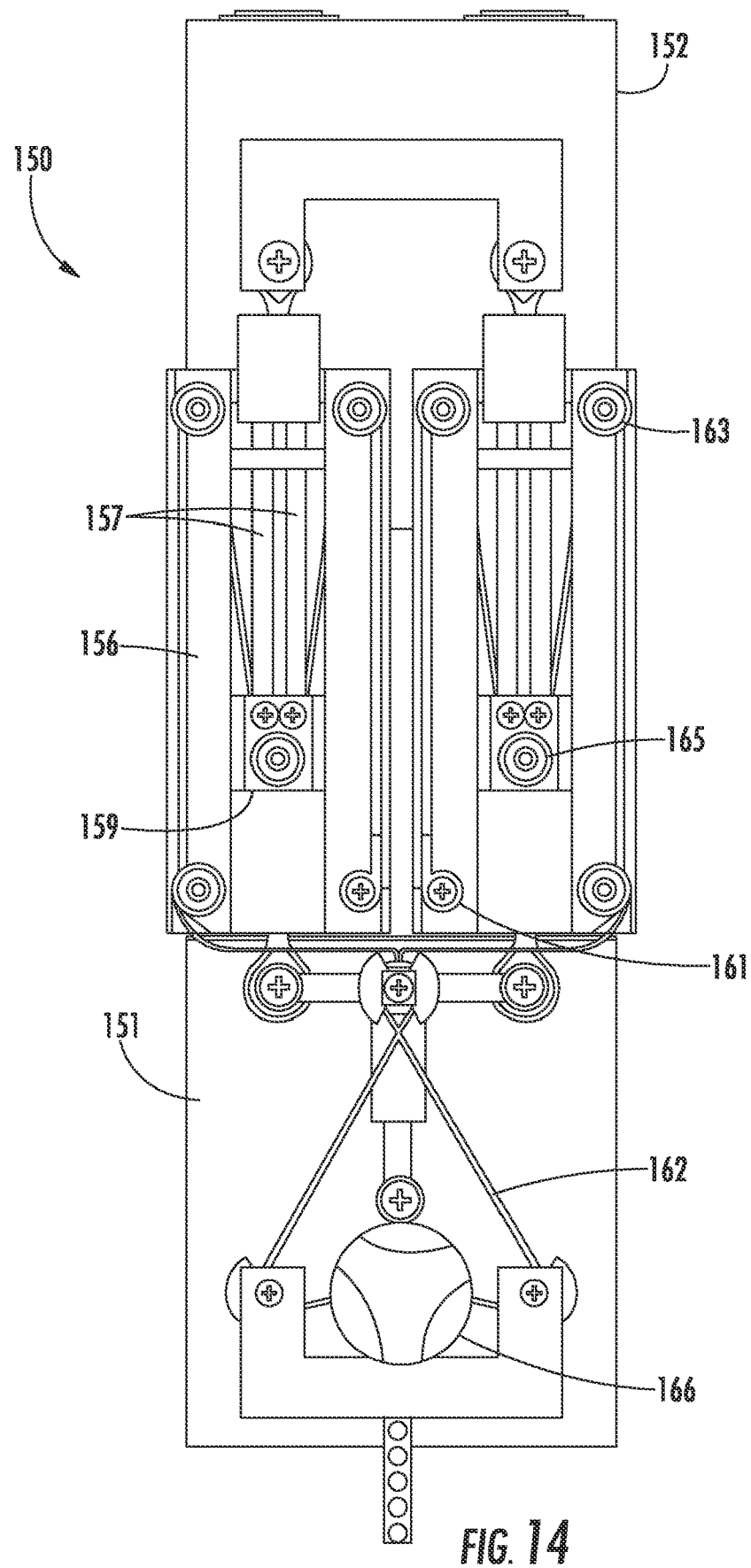
FIGS. 14 through 16 are front views of a distractive force mechanism of a distractive mobility-enabling orthosis according to various alternative embodiments of the presently disclosed subject matter.

As discussed above, the features of distractive force mechanism 150 can be applied to any of a variety of different configurations in addition to the configuration illustrated and described with respect to FIGS. 6 though 12. For example, a variant of distractive force mechanism 150 is illustrated in FIG. 14 in which biasing element 161 and first pulley assembly 163 are embedded inside both of housing 156 of mechanical actuator 153 and channel slot nut 159, and tensioning-adjustment mechanism 166 is positioned on pelvic belt assembly 151. In some embodiments, a case can be placed over housing 156 to keep all of the components inside mechanical actuator 153.

Figure 15:
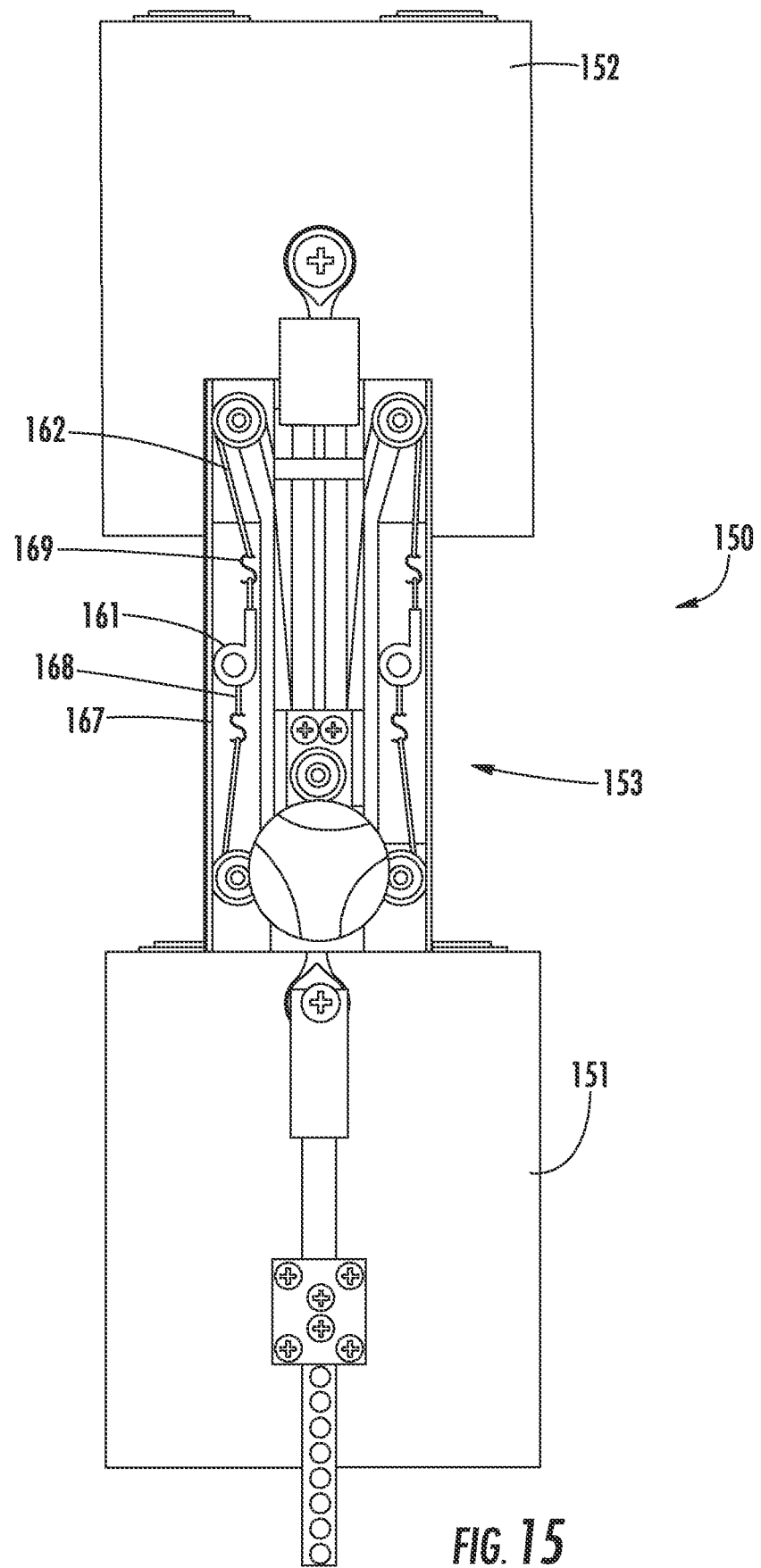

In yet a further alternative embodiment illustrated in FIG. 15, distractive force mechanism 150 is configured to allow biasing element 161 to translate freely inside mechanical actuator 153 in the loaded state. In some embodiments, for example, a biasing element box 167 is placed inside mechanical actuator 153 and vertically constrains biasing element 161 within the channel 158. Attachment strings 168 and attachment hooks 169 connect biasing element 161 to cable tensioning system 160. In some embodiments of this variant, one mechanical actuator 153 is used as opposed to two, and tension-adjusting mechanism 166 is placed on mechanical actuator 153.

Figure 16:
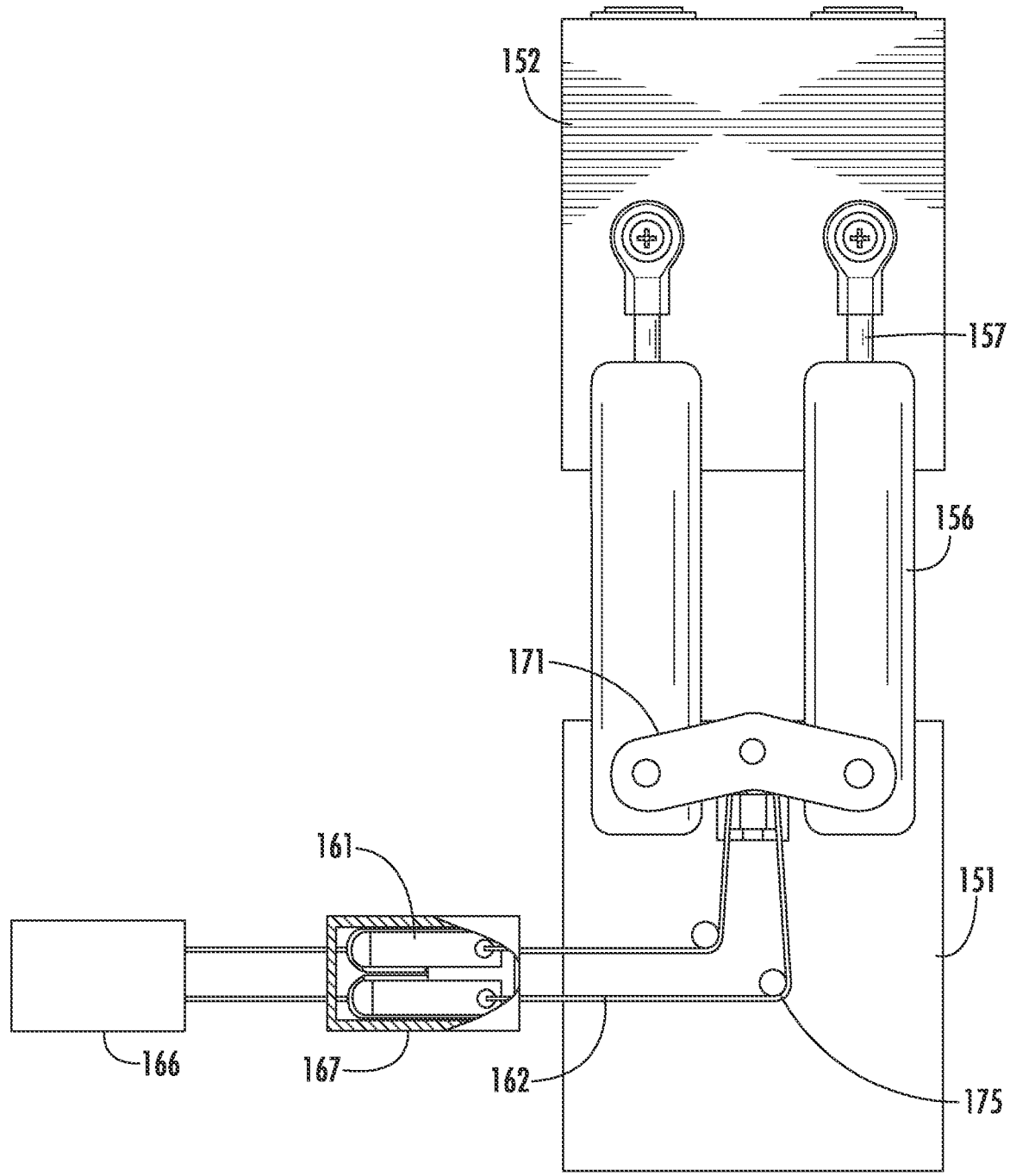

In still a further variant of distractive force mechanism 150 illustrated in FIG. 16, biasing elements 161 can be placed on pelvic belt assembly 151. Also, in some embodiments, housing 156 can have a substantially low-profile design in which rod 157 can freely translate. Instead of first and second pulley assemblies 163 and 165, in some embodiments, ball bearings 175 can be provided around which cable 162 passes. In this configuration, cable 162 passes through rod 157, which allows for translation. The superior and inferior attachments of mechanical actuator 153, such as tie rod ends and/or ball joints, are attached to rod 157 and actuator housing 156, respectively. In this configuration, biasing elements 161 can be positioned outside of housing 156. In the illustrated embodiment, for example, biasing elements 161 are positioned on pelvic belt assembly 151 and are connected to cable 162. In some embodiments, tension-adjustment mechanism 166 comprises a hook-and-loop cinch connected to biasing elements 161, the connection of which can be adjusted to correspondingly adjust the tension and range of motion on biasing elements 161.

With the features discussed above with respect to the above-described embodiment for distractive mobility-enabling orthosis 100, further improvements to the spinal off-loading and bending moments can be realized. For example, the off-loading capacity of distractive mobility-enabling orthosis 100 in this embodiment for a 150 N upper body weight loading condition in the upright stance configuration and through extended ranges of 25° flexion and 10° of extension is given in Table 3 below:

TABLE 3

| Degrees of Rotation | Applied Load (N) | Transferred Load (N) | Brace Load (N) | Brace Load as a Percentage of Applied Load (%) |
|---|---|---|---|---|
| At 10° Extension | 148 | 5 | 143 | 97 |
| At 0° | 143 | 0 | 143 | 100 |
| At 25° Flexion | 139 | -6 | 145 | 104 |

At end range flexion, distractive mobility-enabling orthosis 100 supported the entire applied load and the spine was placed in slight traction (104%). At end range extension, almost the entire applied load was supported by distractive mobility-enabling orthosis 100 (97%). In upright stance, distractive mobility-enabling orthosis 100 supported the entire applied load (100%).

The sagittal bending moment versus angular displacement response of the orthosis is shown for the 150 N upper body weight loading condition in the upright stance configuration and through extended ranges of 25° flexion and 10° of extension in Table 4 below:

TABLE 4

| Degrees of Rotation | Applied Moment (Nm) | Transferred Moment (Nm) | Brace Effect (Nm) | Brace Effect as a Percentage of Applied Moment (%) |
|---|---|---|---|---|
| At 10° Extension | 6.6 | 2.2 | 4.4 | 67% |
| At 25° Flexion | 4.1 | 4.1 | 0 | 0% |

The applied moment required to reach 25° flexion was 4.1 Nm of which distractive mobility-enabling orthosis 100 contributed none of the bending moment (0%). The bending moment required to reach 10° of extension was 6.6 Nm of which distractive mobility-enabling orthosis 100 contributed a little more than half of the bending moment (67%).

Figure 17:
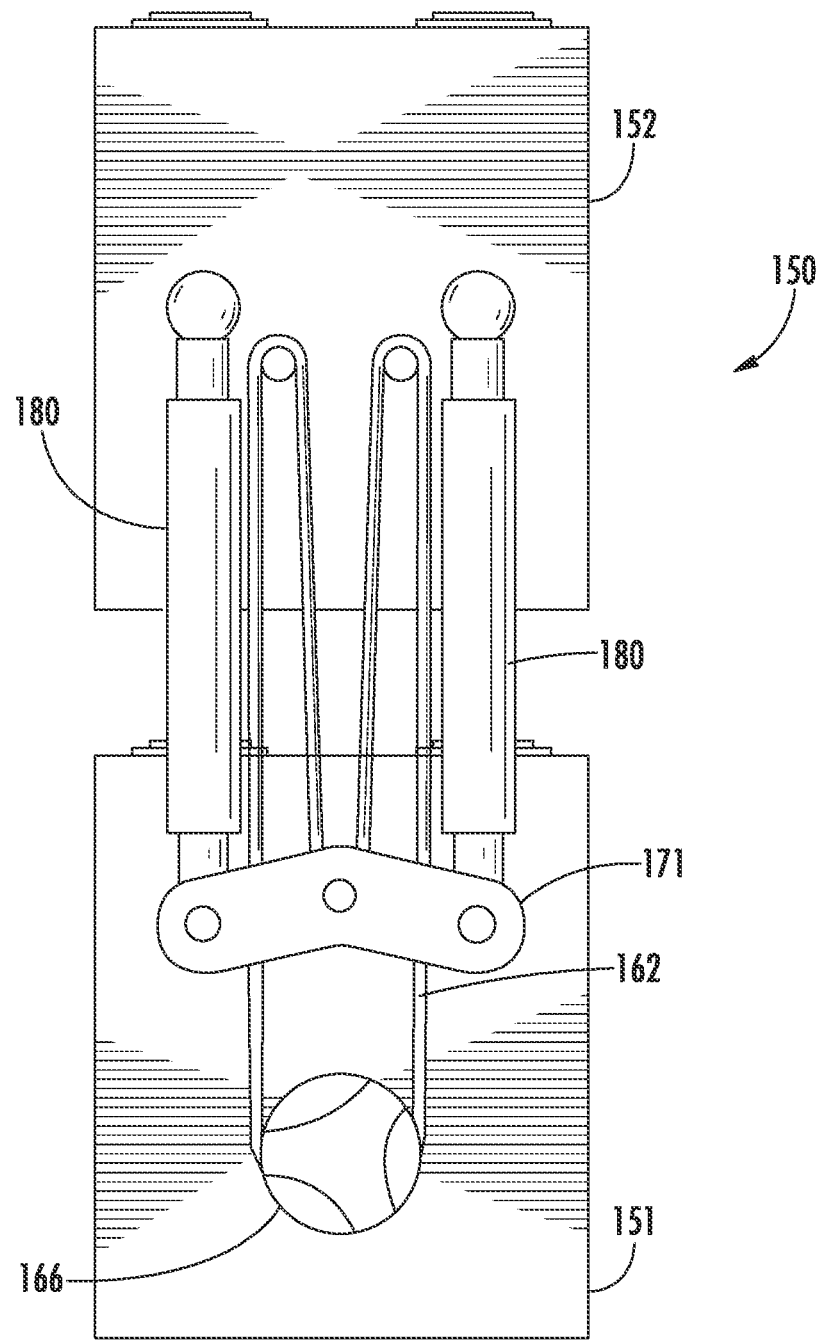
FIG. 17 is a front view of a distractive force mechanism of a distractive mobility-enabling orthosis that incorporates gas struts according to another embodiment of the presently disclosed subject matter.
Figure 18:
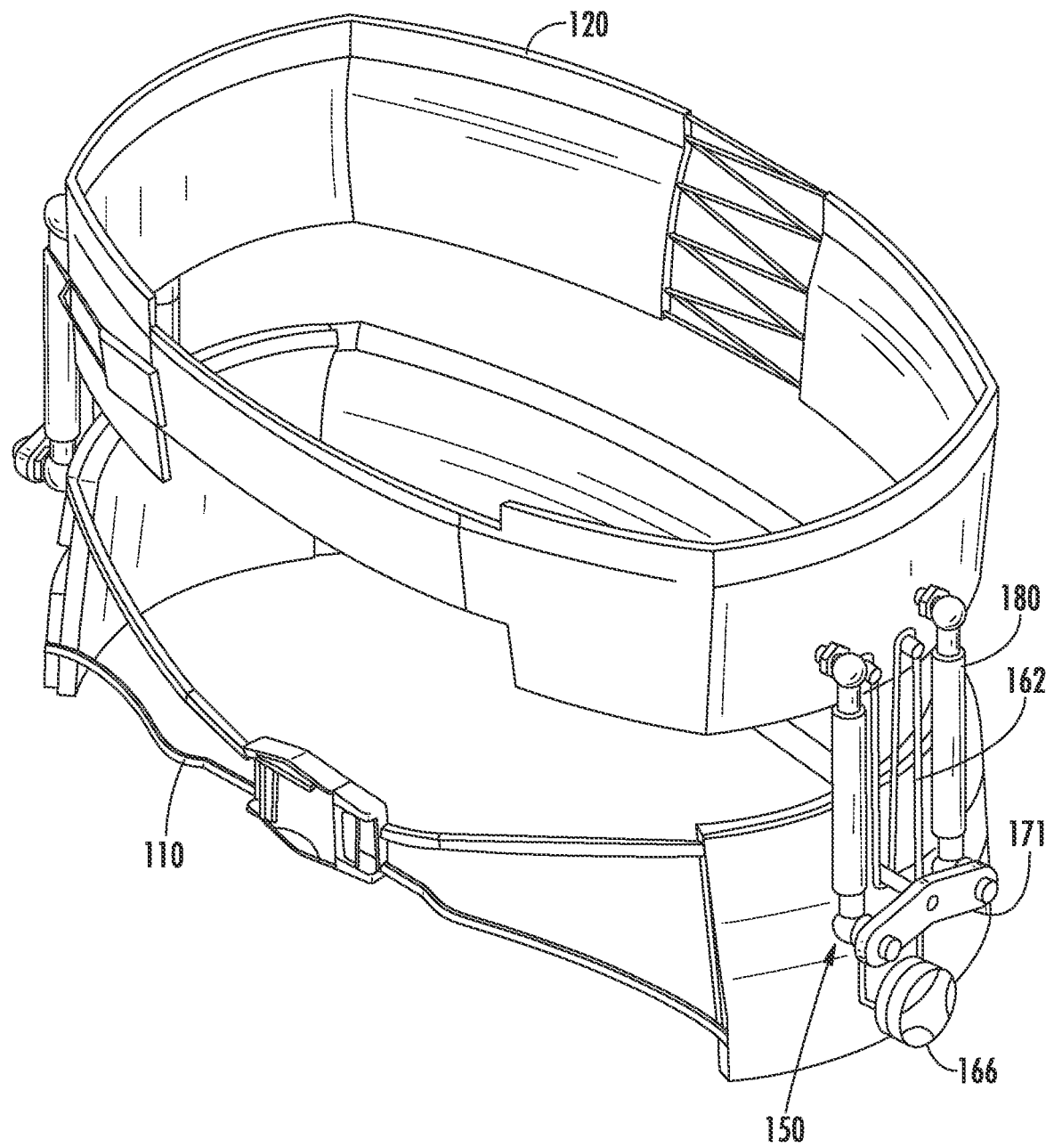
FIG. 18 is a perspective view of a distractive mobility-enabling orthosis that incorporates the gas struts of FIG. 17.

Alternatively, embodiments of the distractive and mobility enabling orthosis shown in FIGS. 17 and 18 implement mechanical actuators 153 of distractive force mechanism 150 as one or more gas struts 180 in place of biasing elements 161 to create the distractive force. Those having ordinary skill in the art will recognize that different force capacity gas struts can be used as the distractive force mechanism that has a variable working stroke. In some embodiments, cable tensioning system 160 can still be connected to each of pelvic belt assembly 151 and torso belt assembly 152, with tension-adjustment mechanism 166 being adjustable to compress gas struts 180 as required for donning and doffing. In some embodiments, attaching gas struts 180 equidistant from the rotational axis of rocker 171 minimizes any additional bending moment from developing within the device that would otherwise have to be overcome by the effort of user to flex or extend the back.

Figure 19:
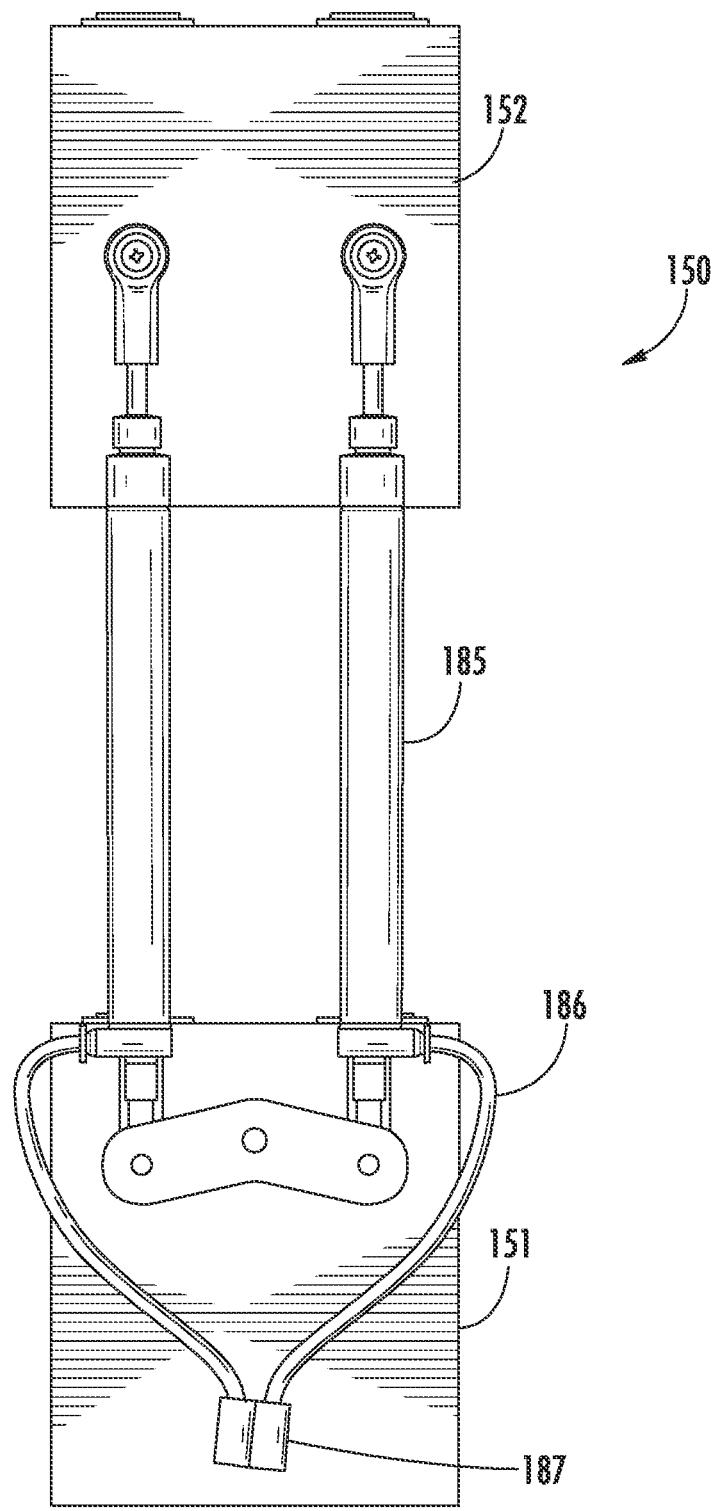
FIG. 19 is a front view of a distractive force mechanism of a distractive mobility-enabling orthosis that incorporates pneumatic cylinders according to another embodiment of the presently disclosed subject matter.
Figure 20:
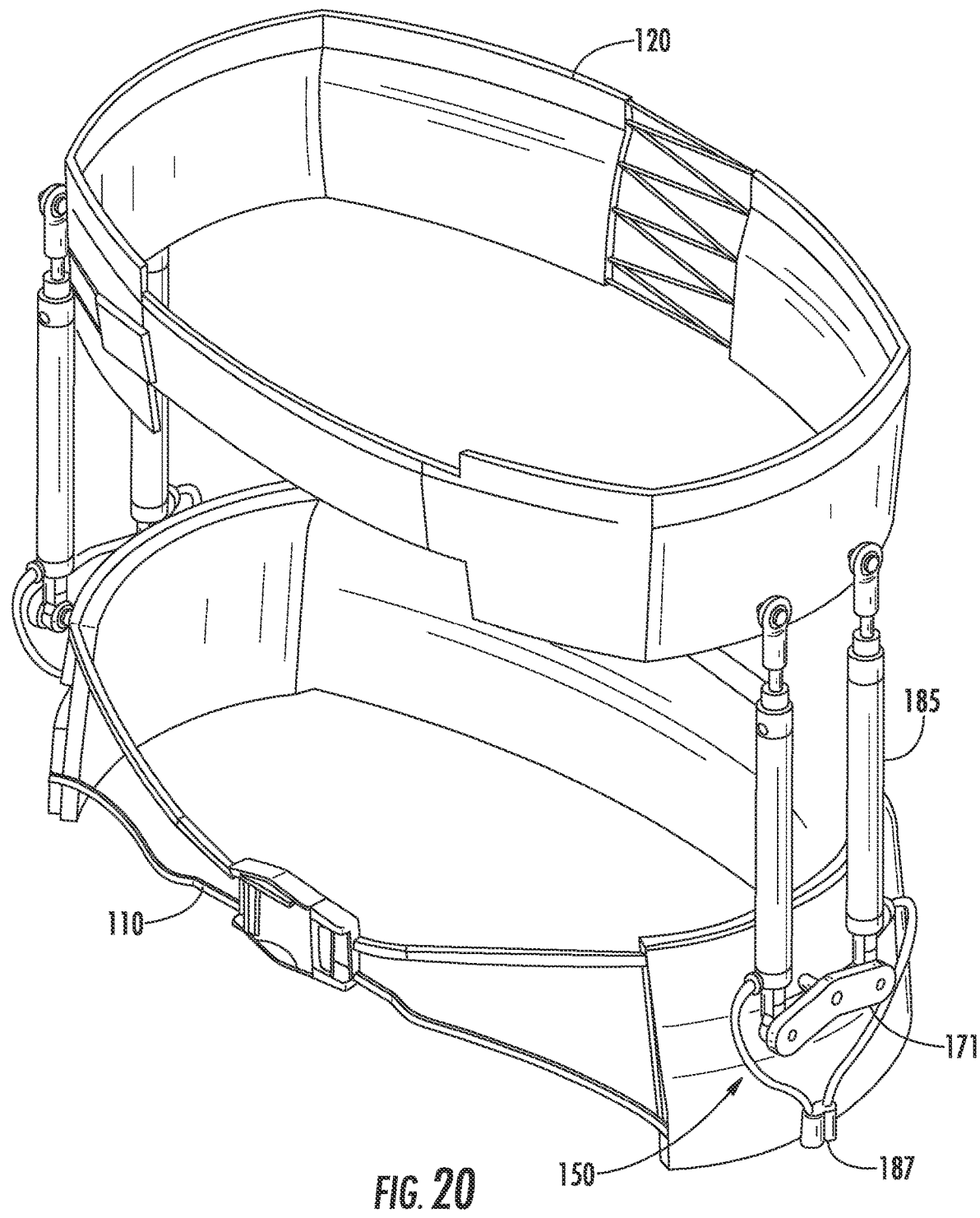
FIG. 20 is a perspective view of a distractive mobility-enabling orthosis that incorporates the pneumatic cylinders of FIG. 19.

In yet a further alternative embodiment shown in FIGS. 19 and 20, distractive force mechanism 150 includes adjustable pneumatic cylinders 185 to create the distractive force.

In each of these embodiments, these cylinders are attached on both sides of the brace and act in series via pneumatic components. In the embodiment illustrated in FIGS. 19 and 20, pneumatic cylinders 185 are connected via tubing 186 and check valves 187 that allow air flow in only one direction so any air introduced into the system will not escape via its entrance route. Those having ordinary skill in the art will recognize that various different pneumatic cylinders can be used to allow for more or less stroke length and force generation.

As discussed herein, the present subject matter discloses a novel lumbar spinal orthosis that provides distractive forces across the lumbar spine and requires minimal effort for movement. This orthosis provides the capability to apply a distractive force to the wearer without losing its output during flexion or extension (and likely axial rotation) by utilizing constant force springs, gas struts, or pneumatic cylinders as the force input into the system. Furthermore, this orthosis was able to meet the specifically chosen design goals such that it properly engaged the wearer, provided a desirable, constant distractive force, allowed mobility, and contained adjustment mechanisms to allow it to be worn by wearers of different sizes.

The present subject matter can be embodied in other forms without departure from the spirit and essential characteristics thereof. The embodiments described therefore are to be considered in all respects as illustrative and not restrictive. Although the present subject matter has been described in terms of certain preferred embodiments, other embodiments that are apparent to those of ordinary skill in the art are also within the scope of the present subject matter.

LIST OF REFERENCES

[1] J. Fritz, "Physical therapy for acute low back pain: associations with subsequent healthcare costs," Spine, vol. 33, pp. 1800-1805, 2008.

[2] D. Akay, "Ant colony optimization approach for classification of occupational low back disorder risks," Hum Factors Ergon Manuf, vol. 19, pp. 1-14, 2008.

[3] L. Brecher, "Editor's Message," JAOA, vol. 101, p. 1, 2001.

[4] P. Pensri, "Biopsychological Factors and Perceived Disability in Saleswomen with Concurrent Low Back Pain," Saf Health Work, vol. 1, pp. 149-157, 2010.

[5] G. Andersson, "Epidemiologic features of chronic low-back pain," Lancet, vol. 354, pp. 581-585, 1999.

[6] R. Deyo, "Low back pain," N Engl J Med, vol. 344, pp. 363-370, 2001.

[7] S. Bigos, "Acute low back problems in adults. Clinical practice guidelines Number 14," P. H. S. US Department of Health and Human Services, Agency for Health Care Policy and Research, Ed., ed, 1994.

[8] A. Tosteson, "The Cost Effectiveness of Surgical versus Non-Operative Treatment for Lumbar Disc Herniation over Two Years: Evidence from the Spine Patient Outcomes Research Trial (SPORT)," Spine, vol. 33, pp. 2108-2115, 2008.

[9] P. Baena-Beato, "Effects of different frequencies (2-3 days/week) of aquatic therapy program in adults with chronic low back pain. A non-randomized comparison trial," Pain Med, vol. 14, pp. 145-158, 2013.

[10] A. Cuesta-Vargas, "Deep water running and general practice in primary care for non-specific low back pain versus general practice alone: randomized controlled trial," Clin Rheumatol, vol. 31, pp. 1073-1078, 2012.

[11] U. Dundar, "Clinical effectiveness of aquatic exercise to treat chronic low back pain: a randomized controlled trial," Spine, vol. 34, pp. 1436-1440, 2009.

[12] Y. Mirovsky, "The effect of ambulatory lumbar traction combined with treadmill on patients with chronic low back pain," J Back Musculoskelet Rehabil, vol. 19, pp. 73-78, 2006.

[13] M. Krag, "Comparison of three lumbar orthoses using motion assessment during task performance," Spine, vol. 28, pp. 2359-2367, 2003.

[14] S. Lantz, "Lumbar spine orthosis wearing. I. Restriction of gross body motions," Spine, vol. 11, pp. 834-837, 1986.

[15] L. Ferrara, "A biomechanical assessment of disc pressures in the lumbosacral spine in response to external unloading forces," Spine J, vol. 5, pp. 548-553, 2005.

[16] D. DiAngelo, "Towards the Design of a Distractive and Mobility-Enabling Back Support Device," Journal of Mississippi Academy of Sciences, vol. 31, pp. 193-200, 2015.

[17] J. Bible, "Normal functional range of motion of the lumbar spine during 15 activities of daily living," J Spinal Disord Tech, vol. 23, pp. 106-112, 2010.

[18] D. DiAngelo, "Robotized Method for Comparative Testing of Back Support Devices," Journal of Mississippi Academy of Sciences, vol. 31, pp. 179-186, 2015.

[19] M. Adams, The Biomechanics of Back Pain vol. 1. Edinburgh, Scotland: Elsevier Science Ltd, 2002.

[20] M. Brown, "Sensory and sympathetic innveration of the vertebral endplate in patients with degenerative disc disease," J Bone Joint Surg, vol. 79, pp. 147-53, 1997.

[21] M. Modic, "Lumbar Degenerative Disk Disease," Radiology, vol. 245, pp. 43-61, 2007.

[22] D. Hoy, "The global burden of low back pain: estimates from the Global Burden Disease 2010 Study," Ann Rheum Dis, vol. 73, pp. 968-974, 2014.

[23] G. Jensen, "Biomechanics of the lumbar intervertebral disk: a review," Phys Ther, vol. 60, pp. 765-773, 1980.

[24] B. Koes, "Diagnosis and treatment of low back pain," BMJ, vol. 332, pp. 1430-1434, 2006.

[25] R. Chou, "Low back pain (chronic)," BMJ Clinical Evidence, vol. 10, pp. 1-41, 2009.

[26] C. Apfel, "Restoration of disk height through non-surgical spinal decompression is associated with decrease discogenic low back pain: a retrospective cohort study," BMC Muscluoskelet Disord, vol. 11, pp. 1-6, 2010.

[27] P. Fritzell, "2001 Volvo Award Winner in Clinical Studies: Lumbar fusion versus nonsurgical treatment for chronic low back pain: a multicenter randomized controlled trial from the Swedish Lumbar Spine Study Group," Spine, vol. 26, pp. 2521-2532, 2001.

[28] J. Brox, "Randomized clinical trial of lumbar instrumented fusion and cognitive intervention and exercises in patients with chronic low back pain and disc degeneration," Spine, vol. 28, pp. 1913-1921, 2003.

[29] G. Kawchuk, "A non-randomized clinical trial to assess the impact of nonrigid, inelastic corsets on spine function in low back pain participants and asymptomatic controls," Spine J, vol. 15, pp. 2222-2227, 2015.

[30] D. Johnson, "Active Spinal Orthosis to Reduce Lumbar Postural Muscle Activity in Flexed Postures," JPO, vol. 28, pp. 109-113, 2016.

[31] J. Cannon, "Evidence on the Ability of a Pneumatic Decompression Belt to Restore Spinal Height Following an Acute Bout of Exercise," JMPT, vol. 39, pp. 304-310, 2016.

[32] P. Leake. vertecorelift. Available: https://vertecorelift.wordpress.com/how-vertecore-lift-works/

[33] J. Simmons, "Development of a Mobility-Enabling Spinal Orthosis and Methods for Evaluating and Developing Spinal Orthoses on a Robotic Platform," PhD, UTHSC Orthopedic Surgery & Biomedical Engineering, The University of Tennessee Health Science Center, 2014.

[34] D. Winter, Biomechanics of Human Movement. New York: Wiley, 1979.

[35] J. Stubbs, "Use of a multi-axis robotic testing platform to investigate the sagittal mechanics of the multi-body lumbar spine," Master of Science, Department of Orthopaedic Surgery and Biomedical Engineering, The University of Tennessee Health Science Center, 2014.

[36] B. Kelly, "A Multiaxis Programmable Robot for the Study of Multibody Spine Biomechanics Using a Real-Time Trajectory Path Modification Force and Displacement Control Strategy," J Med Devices, vol. 7, pp. 1-7, 2013.

[37] I. Gilad, "A study of vertebra and disc geometric relations of the human cervical and lumbar spine," Spine, vol. 11, pp. 154-157, 1986.

[38] J. Crisco, "Optimal marker placement for calculating the instantaneous center of rotation," J Biomech, vol. 27, pp. 1183-1187, 1994.

[39] J. Childs, "Responsiveness of the Numeric Pain Rating Scale in Patient with Low Back Pain," Spine, vol. 30, pp. 1331-1334, 2005.

[40] O. Hägg, "The clinical importance of changes in outcome scores after treatment for chronic low back pain," Eur Spine J, vol. 12, pp. 12-20, 2003.

[41] D. DiAngelo, "A novel distractive and mobility-enabling lumbar spinal orthosis," Journal of Rehabilitation and Assistive Technologies Engineering, vol. 3, pp. 1-10, 2016.

[42] (2013). Medical Coverage Policy: Thoracic Lumbosacral Orthosis with Pneumatics.

What is claimed is:

1. A lumbar spinal orthosis system comprising:
a torso belt configured to be secured about a torso of a user;
a pelvic belt configured to be secured about a pelvis of the user; and
a distractive force mechanism connected between the torso belt and the pelvic belt, wherein the distractive force mechanism is configured to generate a force over a range of displacement between the torso belt and the pelvic belt acting bi-directionally across a lumbar spine of the user to substantially offload bodyweight of the user passing through the lumbar spine;
wherein the distractive force mechanism comprises a mobility enabling component that is configured to allow one or more of flexion, extension, and axial rotation of the torso belt relative to the pelvic belt without substantial resistance.

2. The lumbar spinal orthosis system of claim 1, wherein the distractive force mechanism comprises:
a torso belt assembly coupled to the torso belt;
a pelvic belt assembly coupled to the pelvic belt;
one or more actuators comprising a first actuator portion pivotally connected to the torso belt assembly and a second actuator portion pivotally connected to the pelvic belt assembly, wherein the first actuator portion is movable relative to the second actuator portion; and
a tensioning system coupled to the one or more actuators and configured to apply a distractive force between the first actuator portion and the second actuator portion to allow substantially unrestricted movement of the first actuator portion relative to the second actuator portion.

3. The lumbar spinal orthosis system of claim 2, wherein the tensioning system comprises:
one or more constant force springs coupled to one of the first actuator portion or the second actuator portion; and
one or more tension cables coupled between an end of a corresponding one of the one or more constant force springs and the other of the second actuator portion or the first actuator portion;
wherein the one or more constant force springs are configured to apply the distractive force between the first actuator portion and the second actuator portion when tension is applied to a corresponding one of the one or more tension cables.

4. The lumbar spinal orthosis system of claim 3, wherein the tensioning system comprises a tension adjustment mechanism that is operable to adjust a working length of the one or more constant force springs over which the distractive force is applied.

5. The lumbar spinal orthosis system of claim 2, wherein the second actuator portion is pivotably connected to the pelvic belt assembly.

6. The lumbar spinal orthosis system of claim 2, wherein the pelvic belt assembly comprises one or more adjustment mechanisms configured to adjust one or more of a height of a rotational axis of the one or more actuators or an angular position of the pelvic belt assembly with respect to the torso belt assembly.

7. The lumbar spinal orthosis system of claim 2, wherein the one or more actuators comprise one or more gas struts or one or more pneumatic cylinders coupled to the torso belt assembly and pelvic belt assembly.

8. The lumbar spinal orthosis system of claim 1, comprising a torso glove configured to be positioned between the torso belt and the torso of the user, wherein the torso glove is configured to engage the torso of the user securely without slipping.

9. The lumbar spinal orthosis system of claim 8, wherein one of a hook portion or a loop portion of a hook-and-loop fastening system is provided on an outer surface of the torso glove;
wherein a complementary one of a loop portion or a hook portion of the hook-and-loop fastening system is provided on an inner surface of the torso belt;
wherein the torso glove and the torso belt are configured to be fastened together by the hook-and-loop fastening system.

10. The lumbar spinal orthosis system of claim 1, wherein the torso belt comprises a moldable foam material that is configured to conform to the torso of the user.

11. The lumbar spinal orthosis system of claim 1, wherein the pelvic belt comprises an iliac pad positioned on each of a left and a right interior lateral side of the pelvic belt, wherein each iliac pad is configured to securely engage an iliac crest of the user.

12. The lumbar spinal orthosis system of claim 1, wherein the pelvic belt comprises a moldable foam material that is configured to conform to the pelvis of the user.

13. The lumbar spinal orthosis system of claim 1, wherein the pelvic belt is connected to the distractive force mechanism by the mobility enabling component.

14. A method for offloading at least a portion of a user's bodyweight at a lumbar spine of the user, the method comprising:
securing a torso belt about a torso of the user;
securing a pelvic belt about a pelvis of the user;
connecting a distractive force mechanism between the torso belt and the pelvic belt; and
generating a force by the distractive force mechanism over a range of displacement between the torso belt and the pelvic belt acting bi-directionally across the lumbar spine of the user to substantially offload bodyweight of the user passing through the lumbar spine;
wherein the distractive force mechanism allows one or more of flexion, extension, and axial rotation of the torso belt relative to the pelvic belt without substantial resistance.

15. The method of claim 14, wherein connecting a distractive force mechanism between the torso belt and the pelvic belt comprises:
coupling a torso belt assembly to the torso belt;
coupling a pelvic belt assembly to the pelvic belt;
connecting a first actuator portion of one or more actuators to the torso belt assembly and connecting a second actuator portion of the one or more actuators to the pelvic belt assembly, wherein the first actuator portion is movable relative to the second actuator portion;
coupling a tensioning system to the one or more actuators; and
applying a distractive force between the first actuator portion and the second actuator portion upon movement of the first actuator portion relative to the second actuator portion.

16. The method of claim 15, wherein coupling the tensioning system to the one or more actuators comprises:
coupling one or more constant force springs to one of the first actuator portion or the second actuator portion; and
coupling one or more tension cables between an end of a corresponding one of the one or more constant force springs and the other of the second actuator portion or the first actuator portion;
wherein the one or more constant force springs apply the distractive force between the first actuator portion and the second actuator portion when tension is applied to a corresponding one of the one or more tension cables.

17. The method of claim 16, comprising adjusting a working length of the one or more actuators over which the distractive force is applied.

18. The method of claim 15, wherein the second actuator portion is pivotably connected to the pelvic belt assembly.

19. The method of claim 15, wherein connecting the second actuator portion of the one or more actuators to the pelvic belt assembly comprises adjusting one or more of a height of a rotational axis of the one or more actuators or an angular position of the pelvic belt assembly with respect to the torso belt assembly.

20. The method of claim 15, wherein the one or more actuators comprise one or more gas struts or one or more pneumatic cylinders coupled to the torso belt assembly and pelvic belt assembly.

21. The method of claim 14, wherein securing a torso belt about a torso of the user comprises molding a moldable foam material of the torso belt to conform to the torso of the user.

22. The method of claim 14, wherein securing a torso belt about a torso of the user comprises:
positioning a torso glove about the torso of the user; and
coupling the torso belt to the torso glove about the torso of the user.

23. The method of claim 14, wherein securing a pelvic belt about a pelvis of the user comprises positioning an iliac pad of the pelvic belt on each of a left and a right interior lateral side of the pelvic belt, wherein each iliac pad is configured to securely engage an iliac crest of the user.

24. The method of claim 14, wherein securing a pelvic belt about a pelvis of the user comprises molding a moldable foam material of the pelvic belt to conform to the pelvis of the user.

* * * * *